(12) United States Patent
Jain et al.

(10) Patent No.: US 11,337,919 B2
(45) Date of Patent: May 24, 2022

(54) MODIFIED RELEASE DRUG POWDER COMPOSITION COMPRISING GASTRO-RETENTIVE RAFT FORMING SYSTEMS HAVING TRIGGER PULSE DRUG RELEASE

(71) Applicant: Tris Pharma, Inc., Monmouth Junction, NJ (US)

(72) Inventors: Paras Rameshlal Jain, Dayton, NJ (US); Sachin Vasant Chaudhari, Monmouth Junction, NJ (US)

(73) Assignee: Tris Pharma, Inc., Monmouth Junction, NJ (US)

( * ) Notice: Subject to any disclaimer, the term of this patent is extended or adjusted under 35 U.S.C. 154(b) by 0 days.

(21) Appl. No.: 16/955,377

(22) PCT Filed: Dec. 18, 2018

(86) PCT No.: PCT/US2018/066303
§ 371 (c)(1),
(2) Date: Jun. 18, 2020

(87) PCT Pub. No.: WO2019/126218
PCT Pub. Date: Jun. 27, 2019

(65) Prior Publication Data
US 2021/0015745 A1 Jan. 21, 2021

Related U.S. Application Data

(60) Provisional application No. 62/607,141, filed on Dec. 18, 2017.

(51) Int. Cl.
*A61K 9/00* (2006.01)
*A61K 31/00* (2006.01)
(Continued)

(52) U.S. Cl.
CPC .......... *A61K 9/0065* (2013.01); *A61K 9/1623* (2013.01); *A61K 9/1635* (2013.01);
(Continued)

(58) Field of Classification Search
CPC .... A61K 31/19; A61K 2300/00; A61K 45/06; A61K 47/585; A61K 9/0065;
(Continued)

(56) References Cited

U.S. PATENT DOCUMENTS 3,138,525 A 6/1964 Koff
3,499,960 A 3/1970 Macek et al.
(Continued)

FOREIGN PATENT DOCUMENTS

WO WO 2007/0013 00 A1 1/2007
WO WO 2007/109104 A3 9/2007
(Continued)

OTHER PUBLICATIONS

Singh et al. (FABAD J. Pharm Sci. 2007;32:91-100) (Year: 2007).*
(Continued)

*Primary Examiner* — Ernst V Arnold
(74) *Attorney, Agent, or Firm* — Howson and Howson LLP; Cathy Kodroff

(57) ABSTRACT

An orally administrable drug powder composition which forms a gastro-retentive RAFT having at least two trigger pulses is provided. The composition contains, at a minimum, (a) at least one drug in an immediate release pulse release form; (b) at least one drug in a delayed trigger release form; (c) at least one non-toxic gas generating agent and (d) a RAFT system, wherein following oral ingestion, the composition provides a self-assembling gastro-retentive RAFT having entrapped therein, the at least one drug of (a) and (b) and the gas generated in situ by the non-toxic gas generating agent, thereby providing a floating gastro-retentive RAFT (Continued)

Figure 1A:
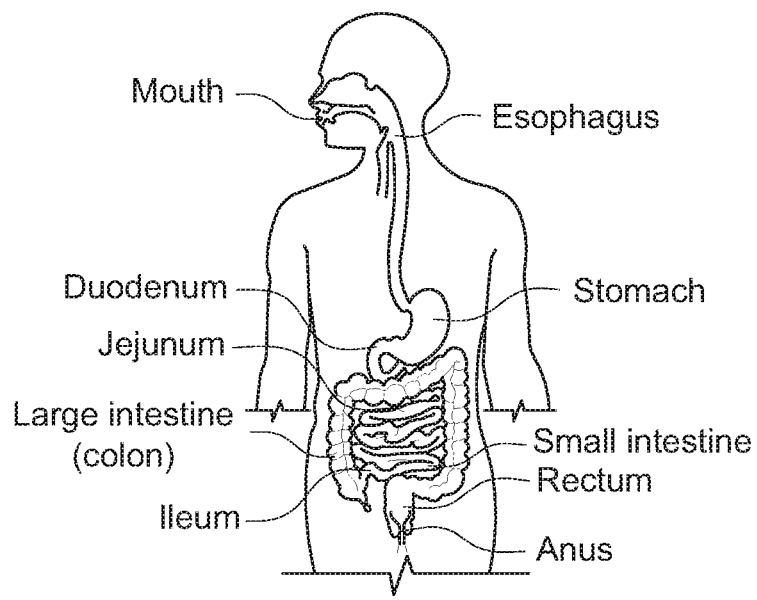

having a dual pulse system wherein at least the second pulse is a trigger pulse and which retains the at least one drug in the stomach for at least about 3 hours, provided that the composition does not include a gamma hydroxybutyrate and its salts, hydrates, tautomers, or solvates, or complexes thereof.

18 Claims, 4 Drawing Sheets

(51) Int. Cl.
  *A61K 47/58* (2017.01)
  *A61K 9/16* (2006.01)
  *A61K 45/06* (2006.01)
(52) U.S. Cl.
  CPC .......... *A61K 9/1652* (2013.01); *A61K 9/1664* (2013.01); *A61K 45/06* (2013.01)
(58) Field of Classification Search
  CPC ...... A61K 9/0095; A61K 9/10; A61K 9/1611; A61K 9/1617; A61K 9/1623; A61K 9/1635; A61K 9/1652; A61K 9/1664; A61K 9/5078; A61K 9/5146
  See application file for complete search history.

(56) References Cited

U.S. PATENT DOCUMENTS

| | | |
|---|---|---|
| 3,901,232 A | 8/1975 | Michaels et al. |
| 4,221,778 A | 9/1980 | Raghunathan |
| 4,352,891 A | 10/1982 | Quinlan |
| 4,393,236 A | 7/1983 | Klosa |
| 4,575,539 A | 3/1986 | DeCrosta et al. |
| 4,847,077 A | 7/1989 | Raghunathan |
| 4,996,047 A | 2/1991 | Kelleher et al. |
| 5,368,852 A | 11/1994 | Umemoto et al. |
| 5,604,927 A | 2/1997 | Moore |
| 5,780,057 A | 6/1998 | Conte et al. |
| 5,808,107 A | 9/1998 | Hollingsworth |
| 5,908,631 A | 6/1999 | Arnaud et al. |
| 5,972,389 A | 10/1999 | Shell et al. |
| 5,980,882 A | 11/1999 | Eichman |
| 5,990,162 A | 11/1999 | Scharf |
| 6,022,562 A | 2/2000 | Autant et al. |
| 6,120,803 A | 9/2000 | Wong et al. |
| 6,187,323 B1 | 2/2001 | Aiache et al. |
| 6,340,475 B2 | 1/2002 | Shell et al. |
| 6,488,962 B1 | 12/2002 | Barner et al. |
| 6,713,639 B1 | 3/2004 | Gurjar et al. |
| 7,294,347 B2 | 11/2007 | Menjoge et al. |
| 7,405,238 B2 | 7/2008 | Markey et al. |
| 7,413,751 B2 | 8/2008 | Devane et al. |
| 7,682,629 B1 | 3/2010 | Besse |
| 7,906,145 B2 | 3/2011 | Castan et al. |
| 7,910,133 B2 | 3/2011 | Castan et al. |
| 7,976,870 B2 | 7/2011 | Berner et al. |
| 8,062,667 B2 | 11/2011 | Mehta et al. |
| 8,193,211 B2 | 6/2012 | Liang et al. |
| 8,202,542 B1 | 6/2012 | Mehta et al. |
| 8,263,650 B2 | 9/2012 | Cook et al. |
| 8,277,843 B2 | 10/2012 | Singh et al. |
| 8,287,848 B2 | 10/2012 | Mehta et al. |
| 8,313,770 B2 | 11/2012 | Pathak et al. |
| 8,318,210 B2 | 11/2012 | Tengler et al. |
| 8,324,275 B2 | 12/2012 | Cook et al. |
| 8,470,375 B1 | 6/2013 | McMahen et al. |
| 8,512,759 B1 | 8/2013 | McMahen et al. |
| 8,586,083 B2 | 11/2013 | Mohammad |
| 8,591,922 B1 | 11/2013 | Allphin et al. |
| 8,592,481 B2 | 11/2013 | Berner et al. |
| 8,668,929 B2 | 3/2014 | Han et al. |
| 8,747,902 B2 | 6/2014 | Mehta et al. |
| 8,778,396 B2 * | 7/2014 | Pillay .................. A61K 31/198 424/469 |
| 8,790,700 B2 | 7/2014 | Mehta et al. |
| 8,802,157 B2 | 8/2014 | Berner et al. |
| 8,859,619 B2 | 10/2014 | Cook et al. |
| 8,901,173 B2 | 12/2014 | Allphin et al. |
| 9,000,046 B2 | 4/2015 | Berner et al. |
| 9,132,107 B2 | 9/2015 | Allphin et al. |
| 9,161,911 B2 | 10/2015 | Hou |
| 9,301,934 B2 | 4/2016 | Berner et al. |
| 9,439,851 B2 | 9/2016 | Dharmadhkari et al. |
| 9,566,258 B2 | 2/2017 | Hou |
| 9,555,017 B2 | 12/2017 | Allphin et al. |
| 10,092,511 B2 | 10/2018 | Castan et al. |
| 10,398,662 B1 | 9/2019 | Allphin et al. |
| 2003/0099711 A1 | 5/2003 | Meadows et al. |
| 2004/0092455 A1 | 5/2004 | Mamelak et al. |
| 2004/0219186 A1 | 11/2004 | Ayres |
| 2005/0136114 A1 | 6/2005 | Kulkarni et al. |
| 2006/0062844 A1 | 3/2006 | Chenevier et al. |
| 2006/0210630 A1 | 9/2006 | Liang et al. |
| 2007/0036843 A1 | 2/2007 | Hirsh et al. |
| 2007/0148239 A1 | 6/2007 | Hall et al. |
| 2007/0215511 A1 | 9/2007 | Mehta et al. |
| 2009/0275530 A1 | 11/2009 | Tester et al. |
| 2012/0076865 A1 | 3/2012 | Allphin et al. |
| 2013/0142846 A1 | 6/2013 | Lee et al. |
| 2016/0128981 A1 | 5/2016 | Chen et al. |
| 2016/0228379 A1 | 8/2016 | Kumar et al. |
| 2016/0317388 A1 | 11/2016 | Bhargava et al. |

FOREIGN PATENT DOCUMENTS

| | | | |
|---|---|---|---|
| WO | WO 2011/119839 A1 | 9/2011 | |
| WO | WO 2012/107652 A1 | 8/2012 | |
| WO | WO 2013/188413 A1 | 12/2013 | |
| WO | WO-2013188413 A1 * | 12/2013 | ............. E21B 43/26 |
| WO | WO2015/166473 A1 | 11/2015 | |
| WO | WO 2015/186108 A1 | 12/2015 | |
| WO | WO 2016/066256 A1 | 5/2016 | |
| WO | WO 2016/087952 A1 | 6/2016 | |
| WO | WO 2019/126214 A1 | 6/2019 | |
| WO | WO 2019/126215 A1 | 6/2019 | |
| WO | WO 2019/126216 A1 | 6/2019 | |

OTHER PUBLICATIONS

Thakral et al. (Expert Opinion on Drug Delivery 2013;10(1):131-149). (Year: 2013).*
Prajapati et al. (Journal of Controlled Release. 2013;168:151-165) (Year: 2013).*
Banerjee S et al., Investigation on crosslinking density for development of novel interpenetrating polymer network (IPN) based formulation, Journal of Scientific and Industrial Research, 2010, 69(10):777-784.
Bhardwaj V et al., Interpenetrating Polymer Network (IPN): Novel approach in Drug delivery, Int. J. Drug Dev. Res., 4(3), Jul.-Sep. 2012.
Bhardwaj L et al., A Short Review on Gastro Retentive Formulations for Stomach Specific Drug Delivery: Special Emphasis on Floating In situ Gel Systems, African J of Basic & Applied Sciences, 2011, 3(6):300-312.
Hanninen K et al., Mechanistic evaluation of factors affecting compound loading into ion-exchange fibers, Eur. J. Pharm. Sci., 2007, 31(5): 306-317.
Koul V et al., Interpenetrating polymer network (IPN) nanogels based on gelatin and poly(acrylic acid) by inverse mini-emulsion technique: synthesis and characterization, Colloids Surf. B. Biointerfaces, 2011, 83(2):2014-213.
Koshmala JD et al., Preparation of interpenetrating networks of gelatin and dextran as degradable biomaterials, Biomaterials, 2000, 21(20) :2019-2023.
Landfester K et al., Synthesis of colloidal particles in miniemulsions, Annual Review of Materials Research, 2006, 36:231-279.
Lohani A et al., Interpenetrating Polymer Networks as Innovative Drug Delivery Systems, Journal of Drug Delivery, 2014, 2014:1-11.

(56) References Cited

OTHER PUBLICATIONS

Lu J et al., One-step synthesis of interpenetrating network hydrogels: Environment sensitivities and drug delivery properties, Saudi J. Biol. Sci. 2016, 2016(3):S22-S31.
Nirmal HB et al., In-Situ gel: New trends in Controlled and Sustained Drug Delivery System, Int. J. of PharmTech Research, 2010, 2(2): 1398-1408.
Yashwantrao PA et al., A Raft Forming System: An Novel Approach for Gastroretention, Int. J. Pure App. Biosci., 2015, 3(4):178-192.
Shailaja P et al., A Review on Gastroretentive Drug Delivery System, International Journal of Research and Development in Pharmacy and Life Sciences, 2016, 5(4):2178-2187.
Sharma AR and Khan A, Gastroretentive Drug Delivery System: An Approach to Enhance Gastric Retention for Prolonged Drug Release, International Journal of Pharmaceutical Sciences and Research, 2014, 5(4):1095-1106.
Subrahmanyam PJ, Design and development of guar gum and borax crosslinked guar gum matrix tablets of theophylline for colon specific drug, Journal of Chemical and Pharmaceutical Research, 2012, 4(2):1052-1060.
Rajesh AM et al., Taste masking of ciprofloxacin by ion-exchange resin and sustain release at gastric-intestinal through interpenetrating polymer network, Asian Journal of Pharmaceutical Sciences, 2015, 10(2015):331-340.
Rajesh AM et al., Taste masking of ofloxacin and formation of interpenetrating polymer network beads for sustained release, Journal of Pharmaceutical Analysis, 2017, 7(2017):244-251.
El Nabarawi Ma et al, Formulation, release characteristics, and bioavailability study of gastroretentive floating matrix tablet and floating raft system of Mebeverine HC1, Drug Design, Development and Therapy, 2017, 11:1081-1093.
Shah SH et al., Stomach Specific Floating Drug Delivery System: A Review, International Journal of PharmTech Research, 2009, 1(3):623-633.
Gupta KC and Ravi Kumar MNV, Semi-interpenetrating polymer network beads of crosslinked chitosan-glycine for controlled release of chlorophenramine maleate, Journal of Applied Polymer Science, 2000, 76(5):672-683.
Qadri MF et al, Biomedical Applications of Interpenetrating Polymer Network System, Open Pharmaceutical Sciences Journal, 2015, 2: 21-30.
Sperling LH and Hu R, Interpenetrating Polymer Networks, Polymer Blends Handbook, 2003, 417-447.
Klempner et al, Interpenetrating Polymer Networks, Advances in Chemistry; American Chemical Society, 1994, 21-38.
Dolas RT et al, Raft Technology for Gatsro Retentive Drug Delivery, Human Journal, 2015, 3(1):232-252.
Prajapati VD et al, Raft forming system—An upcoming approach of gastroretentive drug delivery system, Journal of Controlled Release, 2013, 168(2):151-165.
Davis SS et al., Transit of Pharmaceutical Dosage Forms Through the Small Intestine, Gut, 1986, 27(8):886-892.
Broughton et al., Gamma-hydroxy-butyrate in the treatment of narcolepsy: a preliminary report, in: Guilleminault et al. (Eds.). Narcolepsy (Advances in sleep research. vol. 3.). Holliswood, NY: Spectrum Publications, pp. 659-667, Jan. 1976.
Flamel Technologies Announces Positive Results of a Second Clinical Trial with Micropump® Sodium Oxybate, Dec. 19, 2014, which reports achieving the objective of one single dose before bedtime.
Frucht et al., A Pilot Tolerability and Efficacy Trial of Sodium Oxybate in Ethanol-Responsive Movement Disorders, Movement Disorders, vol. 20(10):1330-1337, Jun. 2005.
Mamelak et al., The effects of [gamma]-hydroxybutyrate on sleep, Biol Psychiatry, vol. 12(2):273-288, Aug. 1976 (published 1977).
Arora S et al., Floating Drug Delivery Systems: A Review, AAPS PharmScieTech, 2005, 6(3):E372-E390.
Chen Y et al., Cubic and Hexagonal Liquid Crystals as Drug Delivery Systems, BioMed Research International, 2014:1-12.
Jain D et al., Recent technologies in pulsatile drug delivery systems, Biomatter, 2011, 1(1):57-65.
Kumar KK et al., Formulation and evaluation of floating in situ gelling system of losartan potassium, Der Pharmacia Lettre, 2015, 7(1):98-112.
Lam WK et al., Monocarboxylate Transporter-Mediated Transport of Gamma-Hydroxybutyric Acid in Human Intestinal Caco-2 Cells, Drug Metabolism and Disposition, 2010, 3 8(3):441-447.
Liechti ME et al., Pharmacokinetics and pharmacodynamics of gamma-hydroxybutyrate in healthy subjects, British Journal of Clinical Pharmacology, 2016, 81:980-988.
Madan JR et al., Development and evaluation of in situ gel of pregabalin, International Journal of Pharmaceutical Investigation, 2015, 5(4):226-233.
Patel DM et al., Formulation and Evaluation of Floating Oral In Situ Gelling System of Amoxicillin, ISRN Pharmaceutics, 2011.
Sajan J et al., Chromotherapeutics and Chronotherapeutic Drug Delivery Systems, Tropical Journal of Pharmaceutical Research, 2009, 8(5):467-475.
Vijaya C and Goud KS, Ion-activated In Situ Gelling Ophthalmic Delivery Systems of Azithromyin, Indian Journal of Pharmaceutical Sciences, 2011, 73(6):615-620.
Saito S et al., Combination of borane-dimehtyl sulfide complex with catalytic sodium tetrahydroborate as a selective reducing agent for alpha-hydroxy esters, versatile chiral building block from (s)-(-)-malic acid, Chemistry Letters, 1984, 1984:1389-1392.
Jain, U.S. Appl. No. 16/955,392, filed Jun. 18, 2020.
Jain, U.S. Appl. No. 16/955,389, filed Jun. 18, 2020.
Jain, U.S. Appl. No. 16/955,373, filed Jun. 18, 2020.
International Search Report and Written Opinion dated Apr. 2, 2019 in International Patent Application No. PCT/US2018/066299.
International Search Report and Written Opinion dated Apr. 15, 2019 in International Patent Application No. PCT/US2018/066300.
International Search Report and Written Opinion dated Apr. 3, 2019 in International Patent Application No. PCT/US2018/066301.
International Search Report and Written Opinion dated Apr. 3, 2019 in International Patent Application No. PCT/US2018/066303.
Guar, P. et al. Ion Exchange Resins in Gastroretentive Drug Delivery: Characteristics, Selection, Formulation and Applications *International Journal of Pharmacology and Pharmaceutical Sciences*, Dec. 2014, 1: 304-312.
Patil, J. S. et al. Ionotropic Gelation and Polyelectrolyte Complexation: The Novel Techniques to Design Hydrogel Particulate Sustained, Modulated Drug Delivery System: A Review *Digest Journal of Nanomaterials and Biostructures*, Mar. 2010, 5(1):241-248.
Thakral, S. et al. Eudragit®: a technology evaluation *Expert Opinion on Drug Delivery*, Oct. 26, 2012, 10(1): 131-149.
Non-Final Office Action, dated Nov. 10, 2021, issued in U.S. Appl. No. 16/955,373.
Requirement for Unity of Invention, dated Jun. 29, 2021, issued in U.S. Appl. No. 16/955,373.
Non-Final Office Action, dated Jun. 30, 2021, issued in U.S. Appl. No. 16/955,392.
Office Action issued in European Patent Application No. 18834152. 3, dated May 14, 2021.
Office Action issued in European Patent Application No. 18834153. 1, dated May 14, 2021.
Office Action issued in European Patent Application No. 18840118. 6, dated May 31, 2021.

\* cited by examiner

MODIFIED RELEASE DRUG POWDER COMPOSITION COMPRISING GASTRO-RETENTIVE RAFT FORMING SYSTEMS HAVING TRIGGER PULSE DRUG RELEASE

CROSS-REFERENCE TO RELATED APPLICATIONS

This is a National Stage Entry under 35 U.S.C. 371 of International Patent Application No. PCT/US2018/066303, filed Dec. 18, 2018, which claims priority to U.S. Provisional Patent Application No. 62/607,141, filed Dec. 18, 2017. These applications are incorporated by reference herein.

BACKGROUND OF THE INVENTION

Some drug molecules exhibit site specific absorption from upper part of small intestine. These molecules exhibit faster and greater absorption in the upper part of the GI tract (stomach, duodenum and jejunum) and slower and lesser absorption in the lower part of the GI tract (ileum, colon and rectum). For such molecules, traditional long acting liquid dosage forms are likely to show lower bioavailability due to incomplete absorption as the dosage form is likely to transit before completing the drug release and prior to absorption. WO2016087952 A1 relates to a gastro-retentive extended release suspension composition, wherein the composition is reportedly characterized by having no substantial change in the in-vitro dissolution release profile upon storage for at least seven days. The extended release (ER) suspension discussed therein contains an osmogent. The hypertonic condition generated in the suspension base affects the leaching of the active ingredient from the extended release coated cores into the suspension base. Reportedly, this hypertonic condition minimizes leaching of the drug from the ER component and thus provides substantially similar in-vitro extended release of the active ingredient throughout the shelf life of the composition Gastroretentive drug delivery systems based on floating rafts have been described in the literature. Certain raft systems are floating, which contain a polymer and gas generating agent, designed to delay clearance of the raft system from the stomach. Different raft forming approaches discussed in the prior art include: swelling based raft formation, temperature dependent gelling based raft formation, pH dependent gelling agent based raft formation, ionic cross-linking based raft formation [Pawar Ashish Yashwantrao et al, A Raft forming system: A Novel approach for gastro-retention, Int. J. Pure App. Biosci. 3 (4): 2015 (178-192).] However, Raft formation has been applied in drug delivery field with limited success, especially limited success when applied to drug molecules that exhibit site specific absorption in upper part of GI tract and at least one of the following: saturable first pass metabolism in GI tract and liver, very short elimination half-life (<3 hours), used for treating diseases following biological rhythms in the form of long acting liquids.

There is need in art to develop a technique of delivering drug molecules that exhibit site specific absorption in upper part of GI tract and at least one of the following: saturable first pass metabolism in GI tract and liver, very short elimination half-life (<3 hours), used for treating diseases following biological rhythms in the form of long acting powders and/or powders for suspension.

SUMMARY OF THE INVENTION

The present invention provides a composition which can generate two pulses of drug release, first pulse immediately after administration and second pulse 2 to 6 hours after the first pulse, while retaining the dosage form in upper part of GI tract for a longer period of time.

In one aspect, an orally administrable drug powder composition is provided which forms a gastro-retentive RAFT having at least two trigger pulses. The composition comprises: (a) at least one drug in a first pulse; (b) at least one drug in a delayed trigger release form; and (c) a RAFT system, wherein following oral ingestion, the composition provides a self-assembling gastro-retentive RAFT having entrapped therein, the at least one drug of (a) and (b) and the gas generated in-situ by the non-toxic gas generating agent, thereby providing a floating gastro-retentive RAFT having a dual pulse system wherein at least the second pulse is a trigger pulse and which retains the at least one drug in the stomach for at least about 3 hours, provided that the composition does not include a gamma hydroxybutyrate and its salts, hydrates, tautomers, or solvates, or complexes thereof.

In certain embodiments, the composition comprises at least one drug in a first pulse and at least one drug in a pH sigmoidal delayed trigger system. Such a trigger system comprises (a) at least one drug and/or drug-ion exchange resin complex; an organic acid coated with a reverse enteric coat; an optional gas generating agent; an optional bulking agent; and (b) coat comprising at least one pH-independent, water-insoluble, water-permeable diffusion barrier coating polymer, e.g., ammonio Methacrylate Copolymer, Type A (e.g., Eudragit® RL), and ammonio methacrylate copolymer, Type B (e.g., Eudragit® RS)) over the particles of (a), wherein said coat dissolves in the presence of the organic acid of (a), whereby following ingestion in the presence of acid a RAFT comprising a pH sigmoidal delayed trigger for the drug of (a) is formed.

In certain embodiments, the composition comprises at least one drug in a first pulse and least one drug in an erosion delayed trigger system. Such a trigger system comprises: at least one erosion barrier forming polymer; an optional gas generating agent; at least one drug and/or drug-ion exchange resin complex; and an optional bulking agent, whereby in the presence of stomach acid, a RAFT comprising the erosion delayed trigger system for the drug is formed.

In certain embodiments, the composition comprises at least one drug in a first pulse and at least one drug in a pH, swelling delayed trigger system. Such a trigger system comprises: (i) granules comprising at least one pH modifier, at least one swelling agent coated with at least one enteric polymer, (ii) granules of step (i) optionally further coated with reverse enteric coat (e.g., Eudragit® EPO) whereby in the presence of stomach acid, a RAFT comprising the pH-swelling delayed trigger system for the drug of (i) is formed.

In certain embodiments, the composition at least one drug in a first pulse and at least one drug in a swelling delayed trigger system. The trigger system comprises: (i) granules comprising at least one drug and/or drug-ion exchange resin complex, at least one gelling agent, at least one swelling enhancer, an optional gas generating agent which generates gas in the presence of stomach acid, optionally, a bulking agent, and (ii) at least one water permeable diffusion barrier coating over the granules of (i), whereby in the presence of stomach acid, a RAFT comprising the swelling delayed trigger system for the drug of (i) is formed.

In certain embodiments, use of a gastro-retentive RAFT forming composition having at least one drug in first pulse and at least one drug in a trigger pulse release for treating a patient is provided. In certain embodiments, the composition contains one or more drug(s) useful for treating one or more of allergic rhinitis, rheumatoid arthritis and related disorders, asthma, cancer, cardiovascular disease, inflammatory disorders, and ulcers.

These and other advantages of the present invention will be apparent from the following detailed description of the invention.

BRIEF DESCRIPTION OF THE INVENTION

Figure 1B:
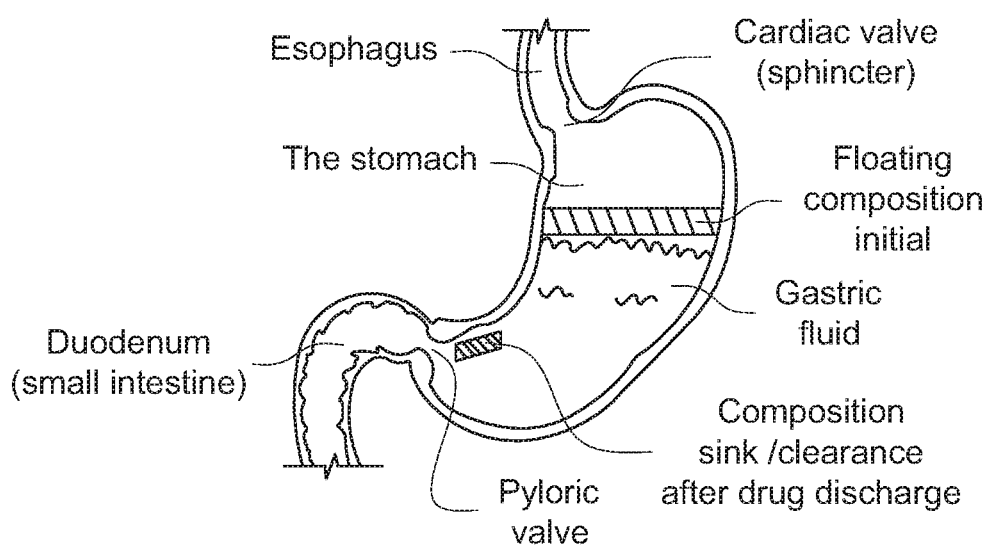

FIGS. 1A and 1B provide schematics of the human gastrointestinal system. FIG. 1A provides an overview of the digestive system, including the stomach, duodenum and jejunum. FIG. 1B provides an enlarged schematic of the stomach, illustrating the entry to the stomach from the esophagus and the exit from the stomach through the pyloric valve into the duodenum. Within the stomach, the floating of the RAFT on the gastric fluid is illustrated at different times post-administration, including "floating" and when it "sinks" following drug release in order to clear through the pyloric valve.

Figure 2:
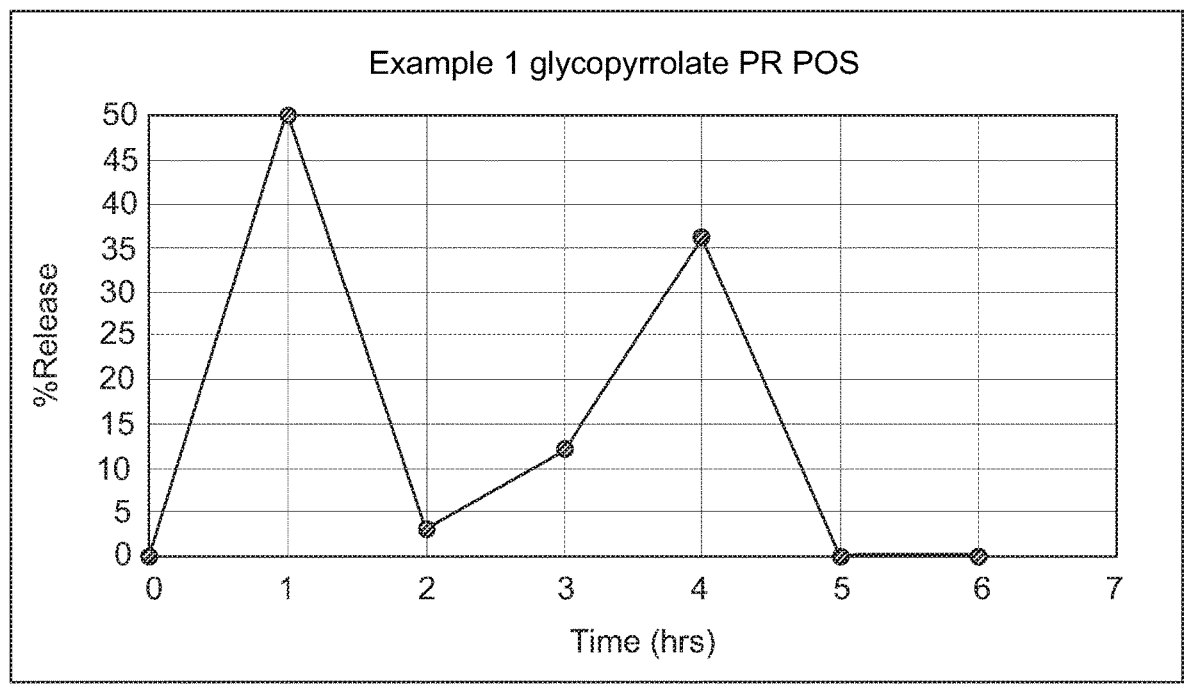

FIG. 2 provides a dissolution profile for an illustrative extended release glycopyrrolate pulse release powder in suspension (POS). Percent (%) cumulative release is graphed against time over a 6-hour test period.

Figure 3:
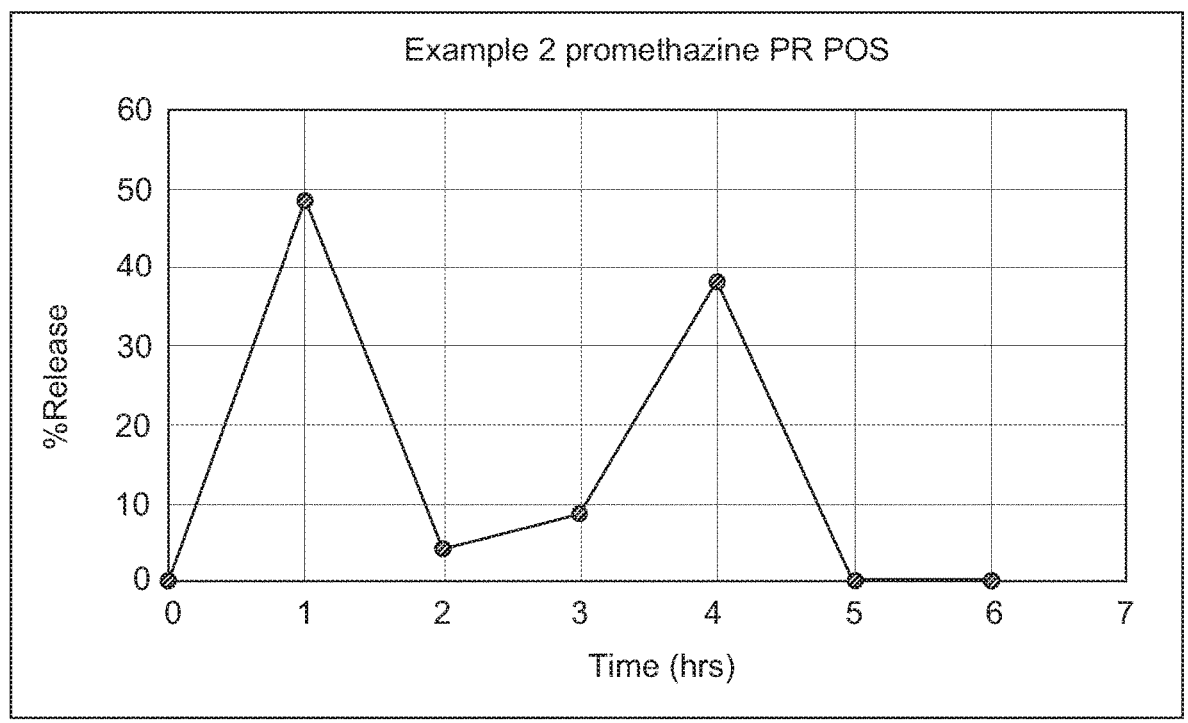

FIG. 3 provides a dissolution profile for an illustrative extended release promethazine pulse release powder in suspension (POS). Percent (%) cumulative release is graphed against time over a 6-hour test period.

Figure 4:
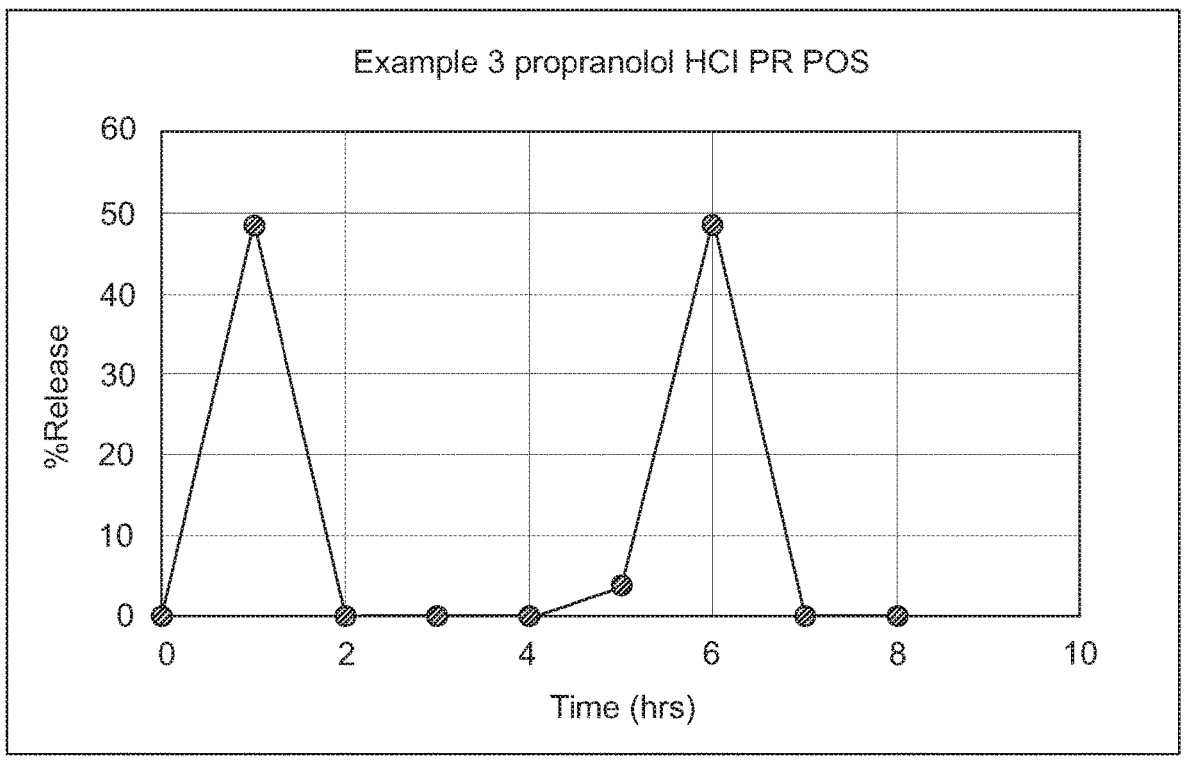

FIG. 4 provides a dissolution profile for an illustrative extended release propranolol pulse release powder in suspension (POS). Percent (%) cumulative release is graphed against time over an 8-hour test period.

Figure 5:
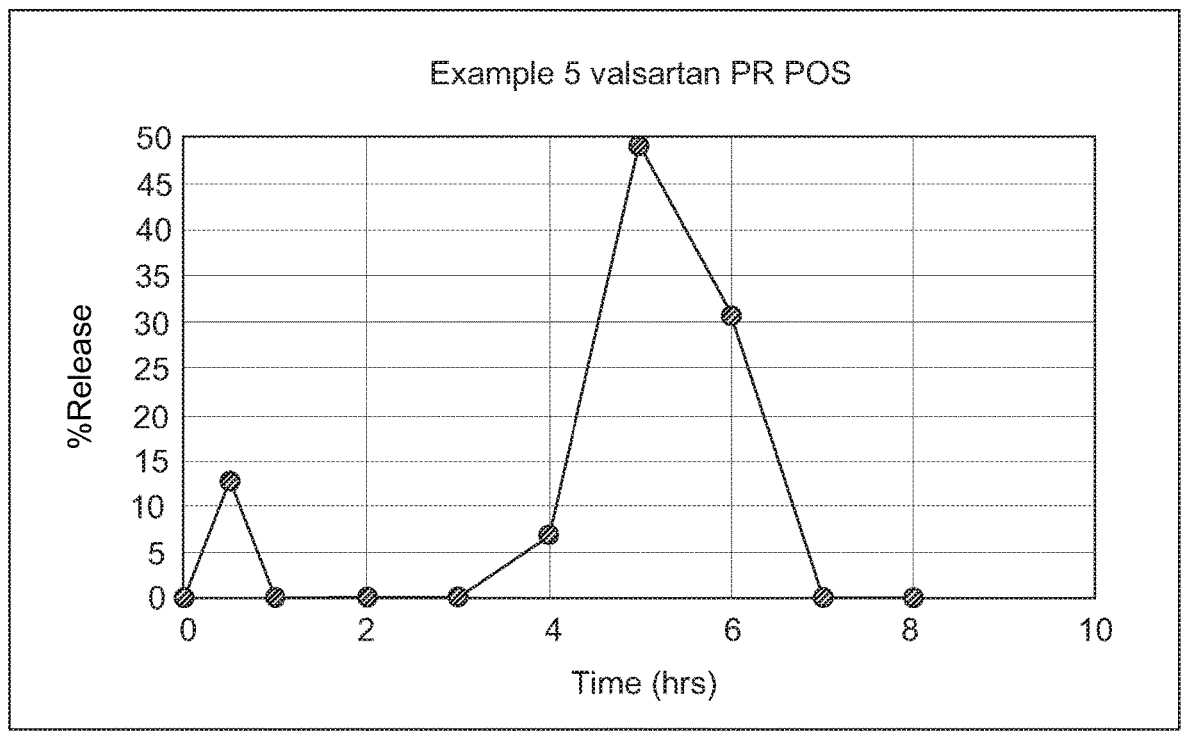

FIG. 5 provides a dissolution profile for an illustrative extended release valsartan pulse release powder in suspension (POS). Percent (%) cumulative release is graphed against time over an 8-hour test period.

Figure 6:
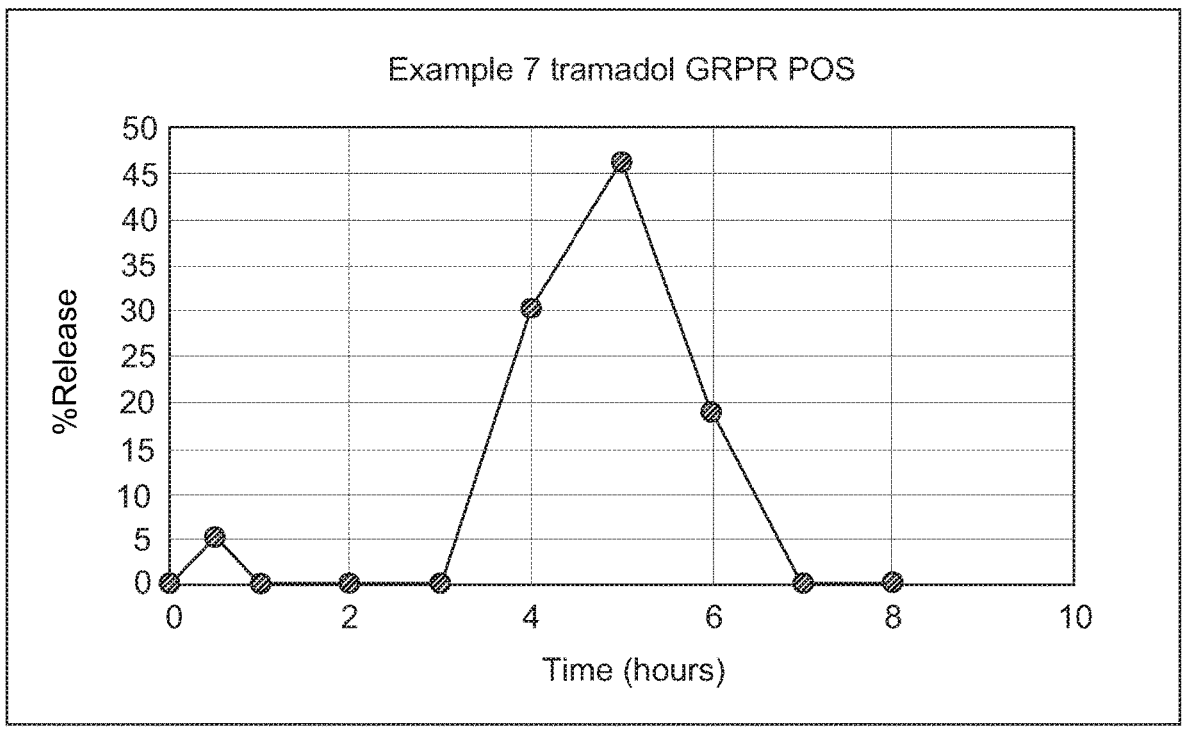

FIG. 6 provides a dissolution profile for an illustrative extended release tramadol pulse release powder in suspension (POS). Percent (%) cumulative release is graphed against time over an 8-hour test period.

DETAILED DESCRIPTION OF THE INVENTION

A gastro-retentive (GR) pulse release (PR) composition as provided herein may be a powder which, post-dosing, provides at least two pulse releases for at least one selected biologically active moiety. The compositions may be reconstituted with water at the time of administration to form suspension or paste or pudding, which might be filled into capsule.

As used herein, the term "biologically active moiety" or "biologically useful moiety" may include an "active pharmaceutical ingredient" or "API), a nutraceutical, a vitamin or other desired moiety. As used herein, an API is any substance or mixture of substances intended to be used in the manufacture of a drug product and that, when used in the production of a drug, becomes an active ingredient in the drug product. Thus, an API may be, e.g., one or more small molecule drugs, cancer therapeutics, or biologics (e.g., hormones, enzymes, peptides, polypeptides, antibodies, antibody fragments, single domain antibody, etc)). Small molecule drugs are generally under about 900 daltons in molecular weight and may be a free base or acid drug or a pharmaceutically acceptable salt, solvate, or hydrate, thereof. In certain embodiments, a biologically useful moiety is in a particle or granule. In certain embodiments, such particles or granules may contain one or more drug-ion exchange resin complexes. In certain embodiments, such particles or granules contain excipients. In certain embodiments, such biologically active moieties (and/or complexes, particles or granules containing same) may be uncoated, or coated with a modified release coating. Unless otherwise specified, where the term "drug" is used in this specification, another biologically active moiety may be substituted. It will further be understood that unless otherwise specified, more than one drug may be used. In certain embodiments, the compositions provided herein do not include a gamma hydroxybutyrate, its salts, hydrates, tautomers, or solvates, or complexes thereof. In certain embodiments, the biologically active moiety is about 0.1 w % to 90 wt %, more preferably about 1 wt % to 75 wt %, or about 15 wt % to 60 wt % based on the total weight of the final dosage form. In certain embodiments, the compositions may include, 0.1 mg to 15 g of active drug(s).

A "drug-ion exchange resin complex" refers to the product resulting from loading at least one drug onto an ion exchange resin. Methods for preparing such complexes have been described, e.g., in WO 2007/109104 and US 2007/0215511A1, incorporated herein by reference. In certain embodiments, this describes the complexation which occurs when the active drug(s) and the ion exchange resin are mixed together in an aqueous medium to facilitate the "exchange" between a salt of the drug and the "ion" of the ion exchange resin and the formation of the complex. Unless otherwise specified, a drug-ion exchange resin complex may be uncoated or coated. In certain embodiments, a drug-ion exchange resin complex may have two or more different drugs complexed to the same ion exchange resin. In certain embodiments, a drug-in exchange resin complex does not contain a gamma hydroxybutyrate, its salts, hydrates, tautomers, or solvates, or complexes thereof.

In certain embodiments, a GR PR composition as provided herein generates a first pulse of drug release within about three hours post-dosing of the composition and at least a second pulse of the drug about 2 hours to about 6 hours after the first pulse.

The term "gastro-retentive" or "GR" as used herein, means post-dosing (e.g., by oral ingestion) at least a portion of the dosed composition remains in the stomach for a period that is longer than the normal emptying time from the stomach, i.e., at least about 2 hours and up to about 24 hours, at least about 3 hours to up to about 24 hours, about 4 hours to about 16 hours, about 5 hours to about 12 hours, or about 6 hours to about 8 hours. Examples of suitable assays for assessing the period of gastric retention are described the examples herein, including the assays for onset and duration of floating in simulated gastric fluid (SGF) without enzyme and integrity/resiliency in SGF. Additionally, a gamma-scintigraphy study may be performed in humans to actually visualization of retention of dosage form in stomach (& upper GIT) along with time for which it remains there will be evaluated. See, e.g., SS Davis, et al, Alimentary tract and pancreas Transit of pharmaceutical dosage forms through the small intestine Gut, 1986, 27, 886-892.

As used herein, a "pulse" refers to a drug release system in which a predetermined amount of a drug is released in a manner that a complete and rapid drug release follows a lag time.

As used herein, a "powder for suspension" or "POS" refers to a composition which is formulated as a powder which designed to be suspended in a suspension base prior to oral ingestion by a patient.

In certain embodiments, the gastro-retentive pulse release (GRPR) POS is particularly well suited for use with a biologically active moiety: (i) that exhibits site specific absorption in upper part of GI tract and saturable metabolism in GI tract and liver; (ii) that exhibits site specific absorption in upper part of GI tract and very short elimination half-life (<3 hours), and/or (iii) that exhibit site specific absorption in upper part of small intestine and are used for treating diseases following biological rhythms. However, other suitable biologically active moieties useful in the invention are described herein and/or will be apparent to one of skill in the art based on the following description.

As used in the preceding paragraph and throughout the specification, the "upper part of the GI tract" for absorption includes the stomach, duodenum and jejunum.

In general, API having solubility or stability problems in the pH conditions of the stomach (under pH 4) are not suitable for the compositions described herein. However, certain uncomplexed drugs may be designed in a drug-ion exchange resin complex, or in a granule, particle or other form as described herein which addresses these solubility or stability issues.

The trigger release mechanisms described herein may be used in combination with a variety of raft forming systems and/or the novel floating IPN forming system described in detail in a US provisional patent application entitled, "Pharmaceutical Compositions Comprising a Floating Interpenetrating Polymer Network Forming System", which is being filed on the same date herewith and which is incorporated herein by reference in its entirely. Such raft systems are described in more detail below.

Pulse Release (PR) of Moiety from GR POS

In certain embodiments, the compositions provided herein are designed to have at least two pulses, a first pulse and at least a second pulse which is a trigger pulse. Optionally, the composition may provide additional pulse releases. Suitably, the ratio of amount of active moiety (e.g., one or more drugs) in the first pulse: amount of active moiety (e.g., one or more drugs) in the second pulse can be from 2:98 to 85:15, based on the weight of the active moiety in its free form (i.e., without including the weight of any salt or complex component). In certain embodiments, the ratio may be about 1:10 to about 10:1, or about 1:1, about 1:20, about 2:1, about 1:4, about 4:1. Values therebetween may be readily selected.

In certain embodiments, the compositions provided herein may have three, or more pulses. In such embodiments, typically the first pulse is instant and at least one other pulse is the trigger release pulse as described herein. In certain embodiments, the compositions provide at least two pulses of the same drug. In other embodiments, the compositions provide two or more drugs, which may be included in at least a first pulse or at least a second pulse. In such instances, the timing of an at least second pulse is determined relative to the timing of a first pulse of the same drug.

A first pulse, as in the instant compositions, may be essentially instantly post-dosing. In certain embodiments, a composition as provided herein provides a drug with a first pulse corresponding to about 10 to about 80% of total dose is formulated as free drug(s), a drug-ion exchange resin complex, and/or a mixture thereof. As described herein, the compositions are designed to provide a first pulse within about 3 hours post-dosing, or within about 2 hours post-dosing, or within about 1-hour post-dosing (e.g., about 10 minutes to 60 minutes).

Compositions provided herein provide at least a second pulse, which uses a trigger mechanism. In certain embodiments, a composition as provided herein provides a drug with the at least second pulse corresponding to about 20 to about 90% of total dose is formulated as trigger principle. Different trigger mechanisms are used for releasing second pulse of API about 2 hours to about 6 hours after the first pulse. The second pulse contain can be achieved by using free drug(s), a drug-ion exchange resin complex, and/or a mixture thereof.

Suitable trigger mechanisms include (a) pH as Trigger: sigmoidal release system, (b) erosion as trigger, (c) pH plus swelling as Trigger for generating second pulse, (d) swelling as trigger, combinations of these systems, and/or combinations of one or more of these systems with other trigger systems such as are identified herein. Such systems are described in more detail below.

It will be noted that for the "first pulse", a biologically active moiety may be provided in any form which is suitable for release in less than about 3 hours, and in certain embodiments, for release in less than about 2 hours, or less than about 1 hour. In certain embodiments, the moiety (e.g., a drug) is delivered as a free base or acid API, or a pharmaceutically acceptable salt thereof. In certain embodiments, the moiety is in a drug-ion exchange complex without a modified release coating. In certain embodiments, the moiety for the first pulse is in a particle, granule, or layered onto a sphere, in the absence of a modified release coating.

Additionally, the compositions provided herein contain at least one biologically active moiety in at least a second pulse form. The following paragraphs describe suitable trigger pulse releases for the at least second pulse forms in the compositions.

As provided herein, a "gas generating agent" refers to an agent that generates nontoxic gas upon contact with gastric fluid. Suitable gas-generating agents include, without limitation, carbonates or bicarbonates of an alkali or alkaline earth metal, such as potassium carbonate or potassium bicarbonate, sodium carbonate or sodium bicarbonate, calcium carbonate, sodium glycine carbonate, magnesium carbonate, and aluminum carbonate; and sulfites such as sodium sulfite, sodium bisulfite, and sodium metabisulfite. These salts may be used alone or in combination with an acid source as a gas-generating couple. The final compositions provided herein include a gas generating agent. The gas generating agent may be present in one or more of the trigger pulse system, the raft forming composition, or admixed with one or more of the other components in the composition. In general, once the gas is entrapped in the GR raft, floating continues as long as integrity of the raft is retained. Thus, same concentration of gas which works for 3-hour (hr) floating is also suitable for longer time periods, e.g., a 12 hr float. In certain embodiments, a gas generating agent is present in concentration range of about 1 w/w to about 25 w/w of the total weight of the GR raft. Suitably, the gas generating agent provides rapid onset (less than about 15 min) and at least or greater than about 3 hr floating. Float may be assessed in vitro using a suitable assay such as those described herein, e.g., in 500 ml simulated gastric fluid without enzymes, and/or other assays known in the art.

Suitably, the GR raft provides a biologically useful moiety (e.g., drug) with a period of retention in the stomach which is longer than the period of time which the moiety would have if administered directly. In certain embodiments, this results in increase bioavailability, absorption, and/or activity in the "gastrointestinal tract" including, the stomach, duodenum, and/or jejunum.

Swelling as Trigger

In certain embodiments, a composition contains at least one biologically active moiety and (i) at least one gelling agent selected from hydrogel forming polymers; (ii) at least one swelling enhancer selected from the following non-limiting list of super-disintegrants; (iii) at least one water permeable diffusion barrier coating; (iv) optionally a gas generating agent; and (v) optionally, a bulking agent, e.g., microcrystalline cellulose (MCC), including e.g., silicified MCC, mannitol, among others.

Granules comprising at least one biologically active moiety (e.g., an API or a drug-ion exchange resin complex, or mixture thereof), gelling agent and swelling enhancer are coated with the diffusion barrier. Without being bound by any theory, it is believed that upon coming into contact with aqueous medium; swelling enhancer causes rapid water uptake. Gelling agent starts forming hydrogel and swelling and starts pushing the coat. Relative proportions of core excipients and coat thickness are optimized such that coat is removed completely due to swelling after 2 and before 6 hrs. Onset of second pulse is tailored by modifying the relative proportions of swelling enhancer and gelling agent and; by modifying the coat thickness. Higher proportion of swelling enhancer and lower portion of gelling agent ensures rapid drug release once coat is removed.

One or more gelling agents are selected from non-limiting list of hydrophilic polymers which form a hydrogel in aqueous medium: carbomers, guar gum, xanthan gum, gum arabic, tragacanth, cellulose polymers and their derivatives (such as, e.g., hydroxypropylmethylcellulose (HPMC), hydroxypropyl cellulose, methylcellulose, and hydroxyethyl cellulose (HEC), carboxymethylethyl cellulose, hydroxyethylmethyl carboxymethyl cellulose, hydroxyethyl methyl cellulose, carboxymethyl cellulose, methylhydroxyethyl cellulose, methylhydroxypropyl cellulose or any mixtures thereof), polysaccharides and their derivatives, polyalkylene oxides, polyethylene glycols, chitosan, poly(vinyl alcohol), xanthan gum, maleic anhydride copolymers, starch-based polymers, crosslinked polyacrylic acids, and combinations thereof.

One or more at least one swelling enhancer, for example, super-disintegrant is selected from non-limiting list of super-disintegrants: crospovidone, SSG, crosslinked sodium carboxymethylcellulose. Swelling enhancer promotes rapid absorption of large amount of aqueous fluid.

At least one water permeable diffusion barrier coating covering the granules comprising API, gelling agent and swelling enhancer. In certain embodiments, the barrier coating adds about 5% w/w to about 80% w/w to the coated granules.

Diffusion barrier coating contains at least one diffusion barrier forming polymer system. Suitable barrier coatings include but are not limited to, water-insoluble release modifiers or water-soluble release modifiers or combinations thereof. The water-insoluble release modifiers that may be employed include polymeric water-insoluble release modifier or non-polymeric water-insoluble release modifier or combinations thereof. Suitable polymeric water-insoluble release modifiers include, but are not limited to, cellulose polymers and derivatives thereof, polyacrylic acid and polymethacrylic acid polymers and derivatives thereof, maleic acid copolymers and derivatives thereof, polyvinyl derivatives; and the like or any combinations thereof. In one embodiment, suitable polymeric water-insoluble release modifiers include, but are not limited to, polyvinyl acetate, polyvinyl chloride, polyvinyl carbonate, ethyl cellulose, nitrocellulose, vinylidene chloride-acrylonitrile copolymer, acrylonitrile-styrene copolymer, ethylene vinyl acetate, cellulose acetate, cellulose acetate phthalate, cellulose acetate butyrate, copolymers of vinyl pyrrolidone, blend of polymers comprising polyvinyl acetate, hydroxypropyl methylcellulose phthalate, methacrylic acid copolymers such as Eudragit® L100/S100/L100-55 and the like or mixtures thereof; methacrylate copolymers such as Eudragit® E100/EPO, Eudragit® RL100/RL30D/RLPO, Eudragit® RS100/RS30D/RSPO and the like or mixtures thereof. Suitable non-polymeric water-insoluble release modifiers include, but are not limited to, fats, oils, waxes, fatty acids, fatty acid esters, glycerides, long chain monohydric alcohols and their esters, phospholipids, terpenes or combinations thereof. Suitable release modifiers in each of these categories have been listed hereinbefore.

In one embodiment, the barrier coating is a pH-independent, water insoluble, water-permeable barrier coating which optionally contains one or more plasticizers, and which is optionally cured. Optionally, the coating includes a plasticizer is used in the percent range, or a mixture of plasticizers combine to total, about 2 to about 50% by weight of the coating layer, more preferably about 2.5% to about 20% by weight of the coating layer on the coated drug-ion exchange resin complex. Preferably a plasticizer in range of about 5% to about 10% by weight of the coating layer based on the coated complex provides the most desirable properties. Suitable plasticizers are water soluble and water insoluble. Examples of suitable plasticizers include, e.g., dibutyl sebacate, propylene glycol, polyethylene glycol, polyvinyl alcohol, triethyl citrate, acetyl triethyl citrate, acetyl tributyl citrate, tributyl citrate, triacetin, and Soluphor P, and mixtures thereof. Other plasticizers are described in Patent Application Publication No. US 2003/0099711 A1, May 29, 2003, page 4 (0041) the disclosure of which is incorporated herein by reference.

In certain embodiments, the pH-independent barrier coating system contains polyvinyl acetate polymer, which in certain embodiments in applied as an aqueous coating dispersion. The polyvinylacetate is insoluble in water at room temperature and may be used in either substantially pure form or as a blend. A commercial blend contains primarily a polyvinyl acetate polymer, a stabilizer, and minor amounts of a surfactant such as sodium lauryl sulfate. More specifically, a desirable aqueous based coating solution is KOLLICOAT® SR30D (BASF Corporation) and whose composition is about 27% polyvinyl acetate, about 2.7% polyvinylpyrrolidone (PVP), about 0.3% sodium lauryl sulfate (solids content 30% w/w). In one embodiment, if a substantially pure form of PVA is used, it can be dissolved in a suitable non-aqueous solvent to provide a coating solution for the drug ion-exchange resin complex. The KOLLICOAT® SR-30D aqueous dispersion may be cured for about 1 to about 24 hours. In alternate embodiments, the coating is cured for about 4 to about 16 hours, and preferably about 5 hours at high temperature, e.g., about 50° C. to about 65° C., and preferably about 60° C. Where the barrier coating comprises polyvinyl acetate, the polyvinyl acetate is present in an amount of about 70% to about 90% w/w of the final barrier coating layer, at least about 75%, at least about 80%, about 85% w/w of the final barrier coating layer. Where the barrier coating also comprises PVP as a stabilizer component (e.g., as is present in KOLLICOAT®™ SR 30D), the final barrier coating layer generally contains about 5 to about 10% w/w of polyvinyl pyrrolidone.

The granules further contain one or more gas generating agents. Gas generating agent generates nontoxic gas upon contact with gastric fluid and is selected from non-limiting list: comprising carbonates or bicarbonates of an alkali or alkaline earth metal such as potassium carbonate or potassium bicarbonate, sodium carbonate or sodium bicarbonate, calcium carbonate, sodium glycine carbonate, magnesium carbonate, and aluminum carbonate; and sulfites such as sodium sulfite, sodium bisulfite, and sodium metabisulfite. These salts may be used alone or in combination with an acid source as a gas-generating couple.

Granules further comprise one or more bulking agent selected from non-limiting list: microcrystalline cellulose, silicified MCC, dicalcium phosphate dehydrate.

Osmosis as Trigger

In certain embodiments, a composition of the invention contains at least one biologically active moiety; (i) at least one gelling agent as defined herein; (ii) at least one osmogent from the non-limiting list of osmogents; (iii) at least one water permeable diffusion barrier coating; (iv) an optional gas generating agent; and (v) optionally, a bulking agent.

Granules comprising at least one biologically active moiety (e.g., at least a drug-ion exchange resin complex), gelling agent and osmogent are coated with the diffusion barrier. Without being bound by any theory, it is believed that upon coming into contact with aqueous medium; the osmogent promotes rapid water uptake. Gelling agent starts forming hydrogel and swelling and starts pushing the coat. Relative proportions of core excipients and coat thickness are optimized such that coat is removed completely due to swelling after 2 and before 6 hrs. Onset of second pulse is tailored by modifying the relative proportions of osmogent and gelling agent and; by modifying the coat thickness. Higher proportion of swelling enhancer and lower portion of gelling agent ensures rapid drug release once coat is removed.

Osmogent promotes rapid absorption of large amount of aqueous fluid. Suitable examples of osmogents or pharmaceutically acceptable inert water-soluble compounds are selected from the group comprising carbohydrates such as xylitol, mannitol, sorbitol, arabinose, ribose, xylose, glucose, fructose, mannose, galactose, sucrose, maltose, lactose, dextrose and raffinose; water-soluble salts of inorganic acids such as magnesium chloride, magnesium sulfate, potassium sulfate, lithium chloride, sodium chloride, potassium chloride, lithium hydrogen phosphate, sodium hydrogen phosphate, potassium hydrogen phosphate, lithium dihydrogen phosphate, sodium dihydrogen phosphate, potassium dihydrogen phosphate, and sodium phosphate tribasic; water-soluble salts of organic acids such as sodium acetate, potassium acetate, magnesium succinate, sodium benzoate, sodium citrate, and sodium ascorbate; water-soluble amino acids such as glycine, leucine, alanine, methionine; urea or its derivatives; propylene glycol; glycerin; polyethylene oxide; xanthan gum; hydroxypropylmethyl cellulose; or mixtures thereof.

Optionally, the granules further comprise of one or more bulking agents, alternatively termed "fillers", such as are described throughout the specification.

In the following illustrative embodiments, the components are provided in percentages reflecting w/w of the trigger system.

pH as Trigger: Sigmoidal Release System:

This pulse trigger system comprises at least one biologically active moiety (e.g, an API, drug-ion exchange resin complex, or mixture thereof) plus: (i) a reverse enteric coated organic acid; (ii) an optional gas generating agent; (iii) optionally a bulking agent; (iii) at least one pH-independent, water-insoluble, water-permeable diffusion barrier coating polymer, e.g., Ammonio Methacrylate Copolymer, Type A (e.g., Eudragit RL), and Ammonio Methacrylate Copolymer, Type B (e.g., Eudragit RS)). In certain embodiments, this pulse trigger system comprises at least one biologically active moiety in the form of drug-ion exchange resin complex (about 60% w/w, 10% w/w to 80% w/w of this pulse trigger system), plus: (i) a reverse enteric coated organic acid (about 8% w/w, 3% w/w to 25% w/w); (ii) an optional gas generating agent (about 5% w/w, 0 to 10% w/w); (iii) optionally a bulking agent (about 5%, 0 to 30% w/w); (iii) at least one pH-independent, water-insoluble, water-permeable diffusion barrier coating polymer, e.g., Ammonio Methacrylate Copolymer, Type B, (about 20%, 10% w/w to 60% w/w). Typically, an organic acid, after granulating with a diluent, is coated with reverse enteric polymer (e.g., Eudragit® EPO). These granules are further mixed with API (and optionally with gas generating agent and bulking agent) and granulated. These granules are coated with a pH-independent water insoluble water permeable diffusion barrier coating polymer (e.g., Eudragit® RS/RL or blend). Without being bound by theory, it is believed that upon coming into contact with Gastric fluid, acidic medium entered into coated particles affects microenvironment pH. This increases permeability of reverse enteric coat on organic acid granules allowing release of organic acid. Based on pKa of organic acid and based on microenvironment pH, organic acid gets dissociated. Dissociated acid reacts with Ammonio Methacrylate Copolymer, Type A, Ammonio Methacrylate Copolymer, Type B or both (Eudragit RS/RL/both) present in the barrier coat and increases permeability of the coat resulting sigmoidal drug release generating the second pulse.

One or more organic acids are selected from non-limiting list: succinic acid, malic acid, fumaric acid, citric acid, tartaric acid and the likes and mixtures thereof.

A reverse enteric coating is pH-dependent and designed not to solubilize or swell in pH greater than about pH 4, or greater than about 4.5. One suitable reverse enteric polymer is an acrylate polymer or copolymer. Particularly suitable reverse enteric coats include those polymers which can be applied as aqueous dispersions. One suitable aqueous dispersion is based on methyl methacrylate and diethylaminoethyl methacrylate copolymer. One example of such a reverse enteric coat is Kollicoat® ® Smartseal 30D, which is an aqueous polymeric dispersion with a solids concentration of approximately 30%. It contains methyl methacrylate and diethylaminoethyl methacrylate copolymer stabilized with approximately 0.6% macrogol cetostearyl ether and 0.8% sodium lauryl sulfate. Still other reverse enteric polymers include, e.g., Eudragit® E 100 (Evonik), Eudragit® EPO (Evonik), methyl methacrylate, hydroxyl ethyl methacrylate and a random terpolymer based on methyl methacrylate, 2-hydroxy ethyl methacrylate and 4-vinylpyridine. The EUDRAGIT® EPO is Poly(butyl methacrylate-co-(2-dimethylaminoethyl) methacrylate-co-methyl methacrylate) 1:2:1 (CAS number: 24938-16-7), i.e., a cationic copolymer based on dimethylaminoethyl methacrylate, butyl methacrylate and methyl methacrylate. The commercial Eudragit® EPO Ready Mix consists of basic butylated methacrylate copolymer, sodium lauryl sulphate, stearic acid and talc. However, other surfactants, including other anionic surfactants, may be substituted for sodium lauryl sulfate in other formulations. Examples of suitable surfactants other than the anionic surfactant sodium lauryl sulfate are known to the skilled artisan. Similarly, lubricants other than stearic acid and glidants other than talc are known in the art and may be selected. Still other reverse enteric polymers are described, and may be made, as described, e.g., US 2006/062844 (2006); US 2005/0136114, U.S. Pat. No. 7,294,347, the disclosure of which is incorporated herein by reference. Weight percentages of these coatings, when present, are provided as weight added, in an amount of about 5% to about 60%, or about 5% to about 20%, or about 8 to about 12% weight added. In certain embodiments, the at least one reverse enteric polymer is selected from Eudragit EPO, Kollicoat® Smartseal 30 D, and uses thereof.

At least one pH-independent, water-insoluble, water-permeable diffusion barrier coating polymer (e.g., Eudragit RS) such as is defined herein covering the granules comprising the biologically active moiety, coated acid, optionally bulking agent and gas generating agent.

Optionally, the granules further comprise of one or more bulking agent.

Erosion as Trigger

In certain embodiments, a composition of the invention includes at least one trigger erosion system. This system comprises: (i) at least one biologically active moiety (e.g., an API, a drug-ion exchange resin complex, or mixture thereof); (ii) at least one erosion barrier forming polymer selected from non-limiting list: HPMC, HEC, other cellulose ethers, guar gum; (iii) an optional gas generating agent; (iv) optionally, bulking agent. Suitably, the active moiety and excipients are coated with the erodible barrier. In certain embodiments, the erosion trigger system comprises (i) at least one biologically active moiety (e.g., an API, drug-ion exchange resin complex, or mixture thereof); (about 60% w/w, 5 w/w to 80%/w/w) (ii) at least one erosion barrier forming polymer selected from non-limiting list: HPMC, HEC, other cellulose ethers, guar gum; (about 15%, 5% w/w to 20% w/w) (iii) an optional gas generating agent (about 7%, 0 to 15% w/w); (iv) optionally, bulking agent (about 15% w/w, 0 to 75% w/w). Suitably, the active moiety and excipients are coated with the erodible barrier.

Without being bound by theory, it is believed that upon coming into contact with aqueous medium; the coat starts eroding. The rate of coat erosion can be tailored by adjusting polymer solubility, viscosity, film thickness. The rate of coat erosion can be tailored by using polymer/s having different solubilities and dissolution rates, for example when working with cellulose ethers, those with small chain length (like ethyl, Hydroxy ethyl cellulose HEC) substitution have greater solubility and faster dissolution rate compared to those with longer chain length substitution (like hydroxyl propyl cellulose). The viscosity of coating polymer plays important role in tailoring coat erosion rate. Greater viscous polymer like HPMC K100M exhibits slower erosion rate compared to low viscosity polymers like HPMC K100LV. Greater coating level, slower is erosion. Thus, for slowing down erosion rate, slowly dissolving (e.g. HPC, HPMC), viscous polymer (viscosity>4000 cps) with higher coating levels (>20% w/w) are selected.

pH Plus Swelling as Trigger

In certain embodiments, a composition of the invention includes granules containing, at a minimum: (i) at least one biologically active moiety (e.g., a drug, drug-ion exchange resin complex, or mixture thereof), (ii) at least one pH modifier; (iii) optionally a swelling agent. The granule is coated with at least one enteric polymer and the coated granules are further coated optionally with a reverse enteric polymer. In certain embodiments, a composition of the invention includes granules containing, at a minimum: (i) at least one biologically active moiety (e.g., a drug, drug-ion exchange resin complex, or mixture thereof), (about 40%, 10% w/w to 75% w/w) (ii) at least one pH modifier (about 20%, 5% w/w to 50% w/w); (iii) optionally a swelling agent (about 10% w/w, 5% w/w to −25% w/w). The granules are coated with at least one enteric polymer and the coated granules are further coated optionally with a reverse enteric polymer.

Without being bound by theory, it is believed that alkaline microenvironment pH created by pH modifier results in dissolution of enteric polymer. Swelling further results in eruption of outer coat which also dissolves in surrounding acidic pH. Various approaches may be used to modify the onset of the second trigger pulse between 2 to 6 hours, including, e.g, the level of enteric coat, level of reverse enteric coat, f swelling agent, and pH modifier enables one to tailor the time for second pulse of API release.

A variety of enteric coatings are known and/or commercially available. Such enteric coatings are pH-dependent, being designed to be stable at pH of about 1 to about 3.5 to about 4 which is present in stomach acid to dissolve in the higher small intestine (e.g., about 7 to about 9). Certain pH-dependent (enteric) polymers including, e.g., members of the EUDRAGIT polymer family, e.g., the L, S, and E, polymers and others which are commercially available may be selected.

Compositions as provided herein may contain a combination of a first pulse release system, one or more of the preceding trigger pulse release systems and/or a combination of a first pulse release and one or more of these trigger pulse systems with yet another pulse release system. Such pulse release systems are incorporated into compositions as provided herein with other suitable components.

Components of Gastro-Retentive Raft Pulse Release

In addition to the at least two pulse drug release systems in the compositions of the invention, the compositions further contain, among other components, one or more gastro-retentive raft forming systems. Such raft forming systems are designed to form in vivo (in situ) in the presence of gas and to entrap one or more pulses, at least one of which is a trigger pulse system. Optionally, the first (or immediate release) pulse is provided by the composition but is not entrapped within the raft. A variety of raft forming systems may be selected.

Ionic Cross-Linking Based Raft Forming System

In certain embodiments, an ionic cross-linking based raft forming system is selected. This system comprises: at least one anionic polymer in an amount of about 2% w/w to about 75% w/w, or about 2% w/w to about 50% w/w, or about 5% w/w to about 40% w/w, or about 10% w/w to about 30% w/w, or about 10% w/w to about 75% w/w, or about 15% w/w to about 65% w/w, or about 20% w/w to about 55% w/w, or about 25% w/w to about 45% w/w, of the raft forming system. One or more anionic polymer(s) may be selected from the following non-limiting list: sodium alginate, carrageenan I, pectin, gellan gum, alginic acid, carrageenan k, sodium carboxy methyl cellulose, and/or xanthan gum; at least one cross-linking agent selected from the following non-limiting list of divalent and trivalent metal salts: Calcium salts like calcium carbonate, calcium chloride, calcium gluconate; magnesium salts, ferrous salts, ferric salts, aluminum salts, and/or zinc salts; at least one gas generating agent like sodium bicarbonate, ammonium bicarbonate, calcium carbonate, sodium carbonate which generates carbon dioxide gas upon reacting with acid and/or a sulfite; and optionally, an effervescent couple.

Without wishing to be bound by theory, it is believed that upon coming into contact with acidic medium, the anionic polymer gets crosslinked with cross linking agent. Gas (e.g., carbon dioxide) generated by a gas generating agent after reacting with stomach acid gets entrapped in the crosslinked polymer causing latter to float. Optionally, an effervescent couple is used to liberate carbon dioxide gas.

A variety of anionic polymers may be selected including, e.g., one or more: pectins, alginic acid, gellan gum, carrageenan, and xantham gum, and/or combinations thereof. Pectins are a family of polysaccharides which in which the polymer backbone mainly comprises α-(1-4)-D galacturonic acid residues. Free calcium ions crosslink the galacturonic acid chains and may be included in the formulation for induction of pectin cross-linking. Advantageously, pectin is water soluble, so organic solvents are not necessary in the formulation. Alginic acid is a linear block copolymer polysaccharide consisting of β-D-mannuronic acid and α-L-glucuronic acid residues joined by 1,4-glycosidic linkages. Aqueous solutions of alginates undergo crosslinking with di- and trivalent metal ions by a cooperative process involving consecutive glucuronic residues in the α-L-glucuronic acid blocks of the alginate chain. Gellan gum (commercially available as Gelrite™ or Kelcogel™) is an anionic deacetylated exocellular polysaccharide with a tetrasaccharide repeating unit of one α-L-rhamnose, one β-D-glucuronic acid and two β-D-glucuronic acid residues. Carrageenans are a family of linear sulfated polysaccharides. There are three main varieties of carrageenan, which differ in their degree of sulphation. Kappa-carrageenan has one sulphate group per disaccharide, Iota-carrageenan has two, and Lambda-carrageenan has three. Iota carrageenan is cross linked by divalent cations while kappa carrageenan is cross-linked by monovalent cations. Xanthan gum is anionic polysaccharide composed of pentasaccharide repeat units, comprising glucose, mannose, and glucuronic acid in the molar ratio 2:2:1.

Swelling Based Raft Forming System

In certain embodiments, a composition as provided herein comprises a swelling based raft forming system. This system comprises: (i) at least one swelling agent selected from non-limiting list: pH dependent swelling agent (e.g., like poly (acrylic acid) (PAA) (e.g., Carbopol® 971P), other carbomers, chitosan), pH independent swelling agent (e.g., like polyox, HPMC, other cellulose ether)s; (ii) optionally, at least one gas generating agent; (iii) optionally one or more pH modifiers; (iv) an optional effervescent couple. For example, one swelling raft system comprises: (i) at least one swelling agent (about 30%, 10% w/w to 75% w/w of the raft); (ii) at least one gas generating agent; potassium bicarbonate (about 10%, 5% w/w to about 30% w/w) (iii) optionally one or more pH modifiers; sodium bicarbonate (about 10% w/w, 5 w/w to about 30% w/w). For example, another swelling raft system comprises: (i) at least one swelling agent (about 30% w/w, 10% w/w to about 75% w/w of the raft)(e.g., about 30% Polyox); (ii) at least one gas generating agent (5% w/w to 30% w/w, or about 10%, (e.g, potassium bicarbonate).

Various pH dependent polymers may be used which cause the formation of in situ gel in the system. Various polymers such as PAA (Carbopol®, carbomer) or its derivatives, polyvinylacetal diethylaminoacetate (AEA), mixtures of poly(methacrylic acid) (PMA) and poly(ethylene glycol) (PEG) show change from sol to gel with change of pH. Swelling of hydrogel increases as the external pH increases in the case of weakly acidic (anionic) groups, but decreases if polymer contains weakly basic (cationic) groups. Mixtures of poly(methacrylic acid) (PMA) and poly(ethylene glycol) (PEG) also have been used as a pH sensitive system to achieve gelation. pH sensitive polymer can be neutral or ionic in nature. The anionic networks contain negatively charged moieties, cationic networks contain positively charged moieties, and neutral networks contain both positive and negatively charged moieties. In the case of anionic polymeric network containing carboxylic or sulphonic acid groups, ionization takes place, as the pH of the external swelling medium rises above the pKa of that ionizable moiety.

Carbopol is a mucoadhesive polymer that increases the formulation's mechanical strength, but also increases surface interaction with the ocular tissue and consequently contact time. Carbopol shows a solid-to-gel transition in aqueous solution as the pH is raised above its pKa of about 5.5; therefore, to have an easy administration, an acidic pH would be needed before carbopol phase transition. Chitosan is a cationic polysaccharide consisting copolymers of glucosamine and N-acetyl glucosamine, these are natural polymer obtained by deacetylation of chitin. It is nontoxic, biocompatible, biodegradable polysaccharide and having bioadhesive, antibacterial activity. Chitosan aqueous solution forms a hydrated gel, like precipitate, at pH exceeding 6.2.

Temperature Dependent Gelling Based Raft Forming System

In certain embodiments, the composition comprises a temperature dependent gelling raft forming system. Such a system may comprise (i) optionally at least one gelling agent which gels at 37° C., but which remains dissolved at room temperature (e.g., about 25% w/w to about 80% w/w, 30% w/w to about 75% w/w, or about 40% w/w to about 65% w/w, or about 45% w/w to about 55% w/w, of the raft forming system). Examples of suitable gelling agents may be selected from the following non-limiting list: Xyloglucan, poloxamer 188, Poloxamer 407, and combinations thereof. The system further contains (ii) at least one gas generating agent (e.g., about 10% w/w to about 40% w/w, or about 15% w/w to about 35% w/w, or about 20% w/w to about 30% w/w of the raft forming system) and, additionally, an optional effervescent couple. For example, one temperature dependent gelling based raft forming system comprises poloxamer 407 (about 50%, 25% w/w to 80% w/w of the raft forming system, sodium bicarbonate (about 25%, 10% w/w to 40% w/w). In another example, temperature dependent gelling based raft forming system comprises poloxamer 188 (40%, 205-80% w/w of the raft forming system, sodium bicarbonate (about 25%, 10% w/w to −40% w/w) of the raft forming system.

Xyloglucan is a polysaccharide composed of a (1-4)-β-D glucan backbone chain, which has (1-6)-α-D xylose branches that are partially substituted by (1-2)-β D galactoxylose. When xyloglucan is partially degraded by β-galactosidase, the resultant product exhibits thermally reversible gelation by the lateral stacking of the rod like chains. The sol-gel transition temperature varies with the ° of galactose elimination. It forms thermally reversible gels on warming to body temperature. Its potential application in oral delivery exploits the proposed slow gelation time (several minutes) that would allow in situ gelation in the stomach following the oral administration of chilled xyloglucan solution.

Cross-Linked Galactomannan Based Raft Forming System

In certain embodiments, the composition comprises at least one cross-linked galactomannan based raft forming system. This system typically comprises: (i) at least one galactomannan polysaccharide in a amount of about 30% w/w to about 80% w/w, or about 30% w/w to about 60% w/w, or about 35% w/w to about 55% w/w of the raft forming system which may be selected from the following non-limiting list: guar gum, fenugreek gum, locust bean gum; (ii) at least one cross-linking agent in an amount of about 5% w/w to about 20% w/w, or about 5% w/w to about 15% w/w, or about 10% w/w of the raft forming system which may be selected from the following non-limiting list: borax, glutaraldehyde, divalent metal salts, trivalent metal salts; (iii) optionally at least one gas generating agent in an amount of about 2% w/w to about 20% w/w, or about 2% w/w to about 15% w/w, or about 2% w/w to about 10% w/w, or about 5% w/w to about 20% w/w, or about 10% w/w to about 20% w/w; and (iv) optionally, a pH modifier may be added to promote the galactomannan cross-linking. In certain embodiments, crosslinked galactomannan based raft forming system comprises, guar gum (about 50% w/w, 30% w/w to 80% w/w), borax (about 10%, 6% w/w to 16% w/w), dibasic calcium phosphate dehydrate (about 5%, 2% w/w to 20% w/w). In certain embodiments, crosslinked galactomannan based raft forming system comprises fenugreek gum (about 50%, 30% w/w to 80% w/w), borax (about 10%, 6% w/w to 16% w/w), meglumine (about 5%, 2% w/w to 20% w/w).

Galactomannans are polysaccharides consisting of a mannose backbone with galactose side groups (more specifically, a (1-4)-linked beta-D-mannopyranose backbone with branch-points from their 6-positions linked to alpha-D-galactose, i.e. 1-6-linked alpha-D-galactopyranose). Examples of suitable galactomannans include, in order of increasing number of mannose-to-galactose ratio: fenugreek gum, mannose:galactose~1:1; guar gum, mannose:galactose~2:1; tara gum, mannose:galactose~3:1; locust bean gum or carob gum, mannose:galactose~4:1. These are not limitations on the galactomannans which are useful and which may be obtained from a variety of sources, including those identified below.

| Galactomannans of Leguminosae species | | |
|---|---|---|
| Botanical name | | |
| Subfamily | Species | M/G ratio |
| CAESALPINIACAE | Cassia absus | 3.00 |
| | C. emarginata | 2.70 |
| | C. Fistula | 3.00 |
| | C. teptocarpa | 3.05 |
| | C. maryfandica | 3.76 |
| | C. nodosa | 2.7-3.5 |
| | G. occidentallis | 3.00 |
| | G. tora | 3.00 |
| | Ceratonia silliqua | 3.75 |
| | Caesalphinia cacalaco | 2.50 |
| | C. pulcherima | 2.7 |
| | C. spinosa | — |
| | Cercidium totorreuanum | 3.36 |
| | Delonix regia | 4.26 |
| | Gietitsia amorphoides | 2.5 |
| | G. triacanthos | 3.2 |
| | Gymnociadus dioica | 2.71 |
| | Parkinsonia aculeata | 2.70 |
| MIMOSACEAE | Besmanthus illinoensis | 2.69 |
| | Leucaerta galauca | 1.33 |
| FABACEAE | sophora japonica | 5.19 |
| | Genista raetam | 4.14 |
| | G. scoparia | 1.59 |
| | G. cretica | 1.55-167 |
| | G. foenum-graecum | 1.2 |
| | G. hamosa | 1.17 |
| | G. monspeiiaca | 1.06 |
| | G. polyseraia | 1.13 |
| | G. radiata | 1.17 |
| | Anthyllis vulneraria | 1.33 |
| | Lotus corniculatus | 1.25 |
| | L. pedunculatus | 1.04 |
| | L. scoparius | 1.13 |
| | Alysicarpus vaginalis | 1.14 |
| | Desmodium pulchellum | 2.00 |

TABLE 2

| Galactomannans of non-leguminous plants | | |
|---|---|---|
| Botanical name | | M/G ratio |
| ANNONACEAE | Annnona muricata | 4.46 |
| CONVOLVULACEAE | Convolvulus tricolor | 1.75 |
| | Ipomoea muricata | 1.8 |
| EBENACEAE | Diospyros virginiana | — |
| LOGANIACEAE | Strychnos nux-vomica | — |
| PALMAE | Borassus flabellifer | 2.4 |
| | Cocos mucifera | 2.57 |
| | Aranga saccharifera | 2.26 |
| | Phytelephas macrocarpa | 50 |
| | Hyphaene thebaica | 19 |
| | Phoenix dactylifera | 10 |

Suitable cross-linking agent for use with a galactomannan may selected from the following non-limiting list: borax, glutaraldehyde, boric acid, organotitanates, other organometallic crosslinkers including Zr, Al, Cr, or combinations thereof.

Liquid Crystal Based Raft Forming System.

In certain embodiments, the composition comprises at least one liquid crystal based raft forming system. Such a system typically comprises: (i) at least one liquid crystal forming substance in an amount of about 30% w/w to about 80% w/w, or about 35% w/w to about 70% w/w, or about 40% w/w to about 60% w/w or about 50% w/w of the raft forming system, (ii) at least one gas generating agent in an amount of about 10% w/w to about 25% w/w, or about 15% w/w to about 25% w/w, or about 10% w/w to about 20% w/w, or about 15% w/w) and iii) optionally a diluent. An example of a liquid crystal forming substance includes glyceryl monooleate (GMO, 2,3-dihydroxypropyl oleate). Other suitable liquid crystal forming substances may include, e.g., phytantriol (PT, 3,7,11,15-tetramethyl-1,2,3-hexadecanetriol) and other lipids such as monolinolein, monoelaidin, phosphatidylethanolamine, oleoylethanolamide, phospholipids, PEGylated phospholipids, D-α-polyethylene glycol, alkyl glycerates, and glycolipids; Oleyl glycerate (OG,2,3-dihydroxypropionic acid octadec-9-enyl ester) and phytanyl glycerate (PG, 2,3-dihydroxypropionic acid 3,7,11,15-tetramethyl-hexadecyl ester). In certain embodiments, liquid crystal based raft forming system comprises D-α-polyethylene glycol (TPGS) (about 50% w/w, 30% w/w to about 80% w/w of the raft forming system), sodium bicarbonate (about 15%, 10% w/w to 25% w/w). In certain embodiments, liquid crystal based raft forming system comprises GMO (about 50% w/w, 30% w/w to 80% w/w), sodium bicarbonate (about 15% w/w, 10% w/w to 25% w/w), microcrystalline cellulose (MCC) (about 15%, 10% w/w to about 25% w/w).

In certain embodiments, a composition of the invention may include more than one Raft forming system.

Biologically Active/Useful Moieties

The compositions provided herein may be useful for delivering at least one biologically active moiety. Regardless of the form in which they are to be incorporated in the compositions, the selected biologically useful moieties or their particles, granules, complexes, etc, selected for inclusion in the composition have an average size of less than about 500 microns in size, preferably less than about 425 microns. However, moieties (particles, granules, complexes, etc) having a larger size may be selected depending upon the total weight (dose) being delivered and/or by adjusting the amount of gas generating agent.

A variety of drugs may be selected for use in the compositions of the invention. Particularly suitable drugs include those that exhibit site specific absorption in upper part of GI tract and saturable metabolism in GI tract and liver, drugs that exhibit site specific absorption in upper part of GI tract and very short elimination half-life (<3 hours), and/or drugs that exhibit site specific absorption in upper part of GI tract and are used for treating diseases following biological rhythms.

Examples of conditions or disorders which may benefit from pulsed release include, without limitation, allergic rhinitis, anti-inflammatory disorders (e.g., rheumatoid arthritis and related painful joint disorders), asthma therapy, chemotherapy (anti-neoplastic agents), cardiovascular therapy, and/or ulcer treatments.

Examples of suitable drugs for gastro-retentive pulse release (GRPR) powders, POS, and suspensions comprising at least one drug selected from: dextromethorphan, amphetamine, morphine hydrochloride, tramadol hydrochloride, baclofen, glycopyrrolate, pregabalin, phenylephrine hydrochloride, viloxazine hydrochloride, mazindol hydrochloride, montelukast sodium, lercarnidipine hydrochloride, ofloxacin, levofloxacin, rebamipide, acebutolol, acecamide hydrochloride, aceclofenac, acetophenazine maleate, acetosulfone sodium, acodazole hydrochloride, adatanserin hydrochloride, albuterol hydrochloride, alendronate sodium, alendronic acid, alentemol hydrobromide, aletamine hydrochloride, alfentanil hydrochloride, alosetron hydrochloride, alprenolol hydrochloride, pirenoxines hydrochloride, alrestatin sodium, altanserin tartrate, amantadine hydrochloride, amedalin hydrochloride, amfenac sodium, amifloxacin, amifostine, amikacin, amiloride hydrochloride, aminacrine hydrochloride, aminobenzoate potassium, aminobenzoate sodium, amiprilose hydrochloride, amiquinsin hydrochloride, amlodipine, amobarbital sodium, amodiaquine, amodiaquine hydrochloride, amoxicillin, amphetamine sulfate, amphomycin, amphotericin B, ampicillin, ampiroxicam, ampyzine sulfate, apomorphine hydrochloride, apraclonidine hydrochloride, aprindine hydrochloride, aprosulate sodium, apurinic acid, aspirin, aspoxicillin, atenolol, atorvastatin, azalanstat dihydrochloride, azaloxan fumarate, azanator maleate, azathioprine sodium, azithromycin, azlocillin, azolimine, azosemide, azotomycin, azumolene sodium, bacampicillin hydrochloride, bacitracin, baclofen, balofloxacin, bamethan sulfate, bamifylline hydrochloride, barnidipine, batanopride hydrochloride, batelapine maleate, benapryzine hydrochloride, benazepril hydrochloride, benazeprilat, bendacalol mesylate, benidipine, benoxaprofen, benoxinate hydrochloride, benzethonium chloride, benzetimide hydrochloride, benzilonium bromide, benzindopyrine hydrochloride, benzoctamine hydrochloride, benzydamine hydrochloride, bepridil hydrochloride, betaxolol hydrochloride, bevantolol hydrochloride, bezafibrate, bialamicol hydrochloride, bicifadine hydrochloride, biclodil hydrochloride, bipenamol hydrochloride, biphenamine hydrochloride, bisoprolol, bithionolate sodium, bleomycin sulfate, brifentanil hydrochloride, brompheniramine maleate, buclizine hydrochloride, budesonide, budipine, buformin, bunolol hydrochloride, bupivacaine hydrochloride, buprenorphine hydrochloride, bupropion hydrochloride, buspirone hydrochloride, butabarbital, butaclamol hydrochloride, butedronate tetrasodium, butoprozine hydrochloride, butorphanol, butoxamine hydrochloride, butriptyline hydrochloride, candesartan, candicidin, captopril, carbaspirin calcium, carbenicillin potassium, carbenoxolone sodium, carbidopa, carbidopa-levodopa, carbinoxamine maleate, carbiphene hydrochloride, carbuterol hydrochloride, carphenazine maleate, carprofen, carteolol hydrochloride, carubicin hydrochloride, carumonam sodium, carvedilol, carvotroline hydrochloride, cefaclor, cefadroxil, cefamandole, cefaparole, cefatrizine, cefazaflur sodium, cefazolin, cefbuperazone, cefcapene pivoxil, cefdaloxime pentexil tosilate, cefdinir, cefditoren pivoxil, cefepime, caretaker, cefetecol, cefixime, cefluprenam, cefinenoxime hydrochloride, cefinetazole, cefminlox, cefodizime, cefonicid sodium, cefoperazone sodium, ceforamide, cefoselis, cefotaxime sodium, cefotetan, cefotiam, cefoxitin, cefozopran, cefpimizole, cefpiramide, cefpirome, cefpodoxime proxetil, cefprozil, cefroxadine, cefsulodin, ceftazidime, cefteram, ceftibuten, ceftizoxime sodium, ceftriaxone, cefuroxime, cephacetrile sodium, cephalexin, cephaloglycin, cetaben sodium, cetalkonium chloride, cetamolol hydrochloride, cetirizine, cetophenicol, cetraxate hydrochloride, chlophedianol hydrochloride, chlorhexidine gluconate, chloroprocaine hydrochloride, chlorpheniramine maleate, ciladopa hydrochloride, cilastatin sodium, cinanserin hydrochloride, cinepazet maleate, ciprofloxacin, clavulanate potassium, Clentiazem maleate, clidinium bromide, clinafloxacin, clomipramine hydrochloride, clonidine, cloroperone hydrochloride, clorprenaline hydrochloride, cloxacillin, codeine, colestipol hydrochloride, cyclophenazine hydrochloride, cyclophosphamide, cycloplatam, dapoxetine hydrochloride, darglitazone sodium, desipramine hydrochloride, dexbrompheniramine maleate, dexchlorpheniramine maleate, dexclamol hydrochloride, dexfenfluramine hydrochloride, dextroamphetamine, dextromethorphan, dextrorphan hydrochloride, dextrothyroxine sodium, dexverapamil, diacetolol hydrochloride, diamocaine cyclamate, diapamide, dibenzepin hydrochloride, diclofenac sodium, dicloxacillin, difloxacin hydrochloride, difluanine hydrochloride, dilevalol hydrochloride, diltiazem hydrochloride, dimefline hydrochloride, dimoxamine hydrochloride, dioxadrol hydrochloride, dipivefin hydrochloride, divalproex sodium, dizocilpine maleate, duloxetine hydrochloride, ephedrine, epinephrine, eprosartan, estrazinol hydrobromide, ethacrynate sodium, ethacrynic acid, ethambutol hydrochloride, etodolac, felodipine, fenofibrate, fenoprofen, flurbiprofen, fluvastatin, fluvastatin sodium, foscarnet sodium, furosemide, gabentin, glicetanile sodium, glycopyrrolate, homatropine hydrobromide, hydralazine hydrochloride, hydrocodone bitartrate, hydromorphone hydrochloride, hydroxyamphetamine hydrobromide, hydroxyzine hydrochloride, ibuprofen, imipramine hydrochloride, indolapril hydrochloride, indomethacin sodium, indoprofen, niacinate, isoproterenol hydrochloride, ketoprofen, ketorolac, labetalol hydrochloride, lamotrigine, letimide hydrochloride, levofloxacin, levorphanol tartrate, losulazine hydrochloride, meclofenamate sodium, medazepam hydrochloride, mefenamic acid, mefloquine hydrochloride, memantine hydrochloride, meperidine hydrochloride, metformin, methicillin sodium, methotrexate, methylphenidate hydrochloride, montelukast sodium, morphine, morphine sulfate, nadolol, nafcillin sodium, nafoxidine hydrochloride, nicardipine hydrochloride, nifedipine, norepinephrine bitartrate, ofloxacin, oxprenolol hydrochloride, oxybutynin chloride, oxycodone, oxymorphone hydrochloride, papaverine hydrochloride, pargyline hydrochloride, paroxetine, pemedolac, penicillin G potassium, penicillin G Sodium, penicillin V potassium, phenmetrazine hydrochloride, phenoxybenzamine hydrochloride, phentermine hydrochloride, phenylephrine hydrochloride, phenylpropanolamine hydrochloride, piperacillin sodium, piperamide maleate, pitavastatin, prazosin hydrochloride, pregabalin, promethazine hydrochloride, propafenone hydrochloride, propranolol hydrochloride, pseudoephedrine hydrochloride, desloratadine/pseudoephedrine sulfate, ramipril, remacemide hydrochloride, remifentanil hydrochloride, ropinirole, rosuvastatin, taciamine hydrochloride, tacrine hydrochloride, talampicillin hydrochloride, talopram hydrochloride, tametraline hydrochloride, N Desmethyl tamoxifen hydrochloride, tampramine fumarate, tamsulosin hydrochloride, tandamine hydrochloride, telmisartan, teloxantrone hydrochloride, teludipine hydrochloride, temafloxacin hydrochloride, tiapamil hydrochloride, tiaramide hydrochloride, tioperidone hydrochloride, tiprenolol hydrochloride, tipropidil hydrochloride, tiquinamide hydrochloride, tramadol hydrochloride, tramazoline hydrochloride, trazodone hydrochloride, trazodone-hcl, trebenzomine hydrochloride, trefentanil hydrochloride, trifluoperazine hydrochloride, valproate sodium, valproic acid, valsartan vardenafil, venlafaxine, veradoline hydrochloride, verapamil hydrochloride, verilopam hydrochloride, viloxazine hydrochloride, zofenopril calcium, zolamine hydrochloride, zolazepam hydrochloride. Other suitable drugs will be apparent to one of skill in the art.

One or more drugs may be used in at least one drug-ion exchange resin complex. Typically, this involves exchanging the acid or base salt of the compound (e.g., a drug or mineral) with the counterion from an ion exchange resin. However, zwitterionic or non-salt forms of certain drugs may form a complex with an ion exchange resin complex. Such complexes may contain one or more drugs. In certain embodiments, two or more drug-ion exchange resin complexes having different drugs may be used in a single composition. In certain embodiments, two or more drug-ion exchange resin complexes which are in different release forms, e.g., immediate release, modified release, including different modified release coatings, may be used in a single composition.

Methods of complexing drugs with ion exchange resins is known in the art. For example, suitable methods for preparing such complexes and examples of suitable ion exchange resins are described in U.S. Pat. Nos. 8,062,667, 8,287,848, 8,202,542, which are incorporated herein by reference. Ion exchange resins suitable for pharmaceutical use are typically water-insoluble and comprise a preferably pharmacologically inert organic and/or inorganic matrix containing functional groups that are ionic or capable of being ionized under the appropriate conditions of pH, in order to permit ion exchange with the drug (other moiety) being complexed therewith. The organic matrix may be synthetic (e.g., polymers or copolymers of acrylic acid, methacrylic acid, sulfonated styrene, sulfonated divinylbenzene), or partially synthetic (e.g. modified cellulose and dextrans). The inorganic matrix preferably comprises silica gel modified by the addition of ionic groups. Covalently bound ionic groups may be strongly acidic (e.g., sulfonic acid, phosphoric acid), weakly acidic (e.g., carboxylic acid), strongly basic (e.g., primary amine), weakly basic (e.g. quaternary ammonium), or a combination of acidic and basic groups. In general, the types of ion exchangers suitable for use in ion-exchange chromatography and for such applications as deionization of water are suitable for use in the controlled release of drug preparations. Such ion-exchangers are described by H. F. Walton in "Principles of Ion Exchange" (pp: 312-343) and "Techniques and Applications of Ion-Exchange Chromatography" (pp: 344-361) in Chromatography. (E. Heftmann, editor), van Nostrand Reinhold Company, New York (1975). Ion exchange resins that can be used in the present invention have exchange capacities of about 6 milliequivalents (meq)/gram and preferably about 5.5 meq/gram or below. Typically the size of the ion-exchange particles is from about 5 microns to about 750 microns, preferably the particle size is within the range of about 40 microns to about 250 microns for liquid dosage forms although particles up to about 1,000 micron can be used for solid dosage forms, e.g., tablets, pellets, powders (including powders for suspensions), and capsules. Particle sizes substantially below the lower limit are generally difficult to handle in all steps of the processing. Generally, uncoated drug-ion exchange resin particles will tend to be at the lower end of this range, whereas coated drug-ion exchange resin particles will tend to be at the higher end of this range. However, both uncoated and coated drug-ion exchange resin particles may be designed within this size range.

The most common organic resins used in formulations are cross-linked polystyrene and polymethacrylate polymers. Ion exchange resins are broadly classified into two main categories, as cation exchange resins and anion exchange resins. Cation exchange resins contain anions attached to polymer and active cations. Cation exchange resins are prepared by the copolymerization of styrene and divinyl benzene and have sulfonic acid groups ($-SO_3H$) introduced into most of the benzene rings. Strong cation acid resins are so named because their chemical behavior is similar to that of a strong acid. These resins are highly ionized in both the acid (R—$SO_3H$) and salt ($RSO_3Na$) form of the sulfonic acid group ($-SO_3H$). The hydrogen and sodium forms of strong acid resins are highly dissociated, and the exchangeable $Na^+$ and $H^+$ are readily available for exchange over the entire pH range. Consequently, the exchange capacity of strong acid resins is independent of the solution pH. For example, sodium polystyrene sulfonate USP (Amberlite IRP 69). Weak Acid Cation Exchange Resins: These resins behave similarly to weak organic acids that are weakly dissociated. In a weak acid resin the ionizable group is a carboxylic acid (COOH) as opposed to the sulfonic acid group ($SO_3H$) used in strong acid resins. The degree of dissociation of a weak acid resin is strongly influenced by the solution pH. Consequently, resin capacity depends in part on the solution pH. A typical weak acid resin has limited capacity below a pH of 6.0.

Anion exchange resins can be prepared by first chlormethylating the benzene rings of styrene-divinylbenzene copolymer to attach $CH_2Cl$ groups and then causing these to react with tertiary amines such as triethylamine. A strong base type anion exchange resin is highly ionized and exchange capacity is not affected by pH. In certain embodiments, a strongly basic anion exchanger contains quaternary ammonium groups attached to a styrene and divinylbenzene copolymer. An example of strong base anion exchange resin is cholestyramine. Duolite AP143/1083 is cholestyramine USP supplied by Dow Chemical Company. A weak base type anion exchange resins exhibit minimal exchange capacity above pH 7. An example of a weakly basic anion exchangers contain polyalkylamine groups attached to a styrene and divinyl benzene.

Inorganic ion exchangers include zeolites, which are microporous, aluminosilicate minerals. Zeolites have a porous structure that can accommodate a wide variety of cations, such as Na+, K+, Ca2+, Mg2+ and others. These positive ions are rather loosely held and can readily be exchanged for others in a contact solution. Some of the more common mineral zeolites are analcime, chabazite, clinoptilolite, heulandite, natrolite, phillipsite, and stilbite. An example of the mineral formula of a zeolite is: $Na_2Al_2Si_3O10.2H_2O$, the formula for natrolite.

The selected ion-exchange resins may be further treated by the manufacturer or the purchaser to maximize the safety for pharmaceutical use or for improved performance of the compositions. Impurities present in the resins may be removed or neutralized by the use of common chelating agents, anti-oxidants, preservatives such as disodium edetate, sodium bisulfite, and so on by incorporating them at any stage of preparation either before complexation or during complexation or thereafter. These impurities along with their chelating agent to which they have bound may be removed before further treatment of the ion exchange resin with a granulating agent and optional modified release coating.

Binding of the selected drug or combination of drugs to the ion exchange resin can be accomplished using methods known in the art. The binding may be performed, for example as a batch or column process, as is known in the art. Typically the drug-ion exchange resin complex thus formed is collected by filtration and washed with appropriate solvents to remove any unbound drug or by-products. The complexes can be air-dried in trays, in a fluid bed dryer, or other suitable dryer, at room temperature or at elevated temperature.

In one example, drug-ion exchange resin complex can be prepared by dissolving the drug(s) in deionized water, adding ion exchange resin USP under stirring and continuing stirring further. The stirring is continued further for a period of 15 min to 20 hrs. More preferably, for 30 min to 10 hr, more preferably from 1 hr to 5 hr. In one embodiment, the drug-ion exchange resin complexes can be prepared using methods known in the art, such as, but not limited to, blending, slurrying, kneading, grinding, sieving, filling, compressing, lyophilization, spray-drying, fluid-bed drying or centrifugal granulation. The drug-resin binding may be performed, for example, as a batch or column process, as is known in the art. In one illustrative embodiment, drug-ion exchange resin complex is prepared by batch process. In one embodiment the drug-resin complexes were prepared by stirring aqueous slurry of drug and ion exchange resin for about 0.5 hours to about 12 hours, followed by filtration and drying of the formed drug-ion exchange resin complex. Drug: ion exchange resin by weight ratio in the complex (also termed a resinate) can be from 1:0.1 to 1:100, more preferably from 1:1 to 1:10. The amount of drug that can be loaded onto a resin will typically range from about 1% to about 75% by weight of the drug-ion exchange resin particles. In one embodiment, loading of about 10% to about 40% by weight, more desirably, about 15% to about 30% by weight, of the drug-ion exchange resin particles can be employed. Typical loadings of about 25% by weight of the drug-ion exchange resin particles can be advantageously employed.

Optionally, a drug-ion exchange resin complex may be granulated with a polymer in preparation for formulation and/or for further processing (e.g., coating). Such a polymer may optionally provide modified release properties to the drug(s) in the complex. Suitably, the granulating agent does not form a separate coating layer on the drug-ion exchange resin complex, but forms a matrix therewith. Examples of suitable polymer systems include, for example, a polyvinyl acetate polymer or a mixture of polymers containing same (e.g., KOLLICOAT® SR 30D), cellulose acetates, ethylcellulose polymers (e.g., AQUACOAT™ ECD-30 or SURELEASE™), acrylic based polymers or copolymers (e.g., represented by the EUDRAGIT family of acrylic resins), cellulose phthalate, or any combination of such water-insoluble polymers or polymer systems. One suitable polymer system which may provide release retardant properties is a polyvinyl acetate polymer as described herein or an acrylic polymer from the EUDRAGIT family. Examples of suitable acrylic polymers from the EUDRAGIT family may include, e.g., a copolymer comprising ethyl acrylate and methyl methacrylate (e.g., EUDRAGIT NE-30D), or EUDRAGIT RS, RL30D, RL100, or NE, which are largely pH-independent polymers; although less desirable, certain pH-dependent members of the EUDRAGIT polymer family, e.g., the L, S, and E, polymers may be selected. Examples of polymers and/or polymer systems which do not provide any significant release retardant properties include the impregnating agents described for example in U.S. Pat. No. 4,221,778 and published US Patent Application Publication No. US 2003/009971 A1, the disclosures of which are incorporated herein by reference. Specific examples of suitable impregnating agents include propylene glycol, polyethylene glycol, polyvinyl alcohol, polyvinyl pyrrolidone (e.g., KOLLIDON® K30) mannitol, methyl cellulose, hydroxypropyl methylcellulose, hydroxypropyl cellulose, and sorbitol. The quantity of the granulating agent typically ranges from about 3% to about 30% or more by weight of the uncoated drug-ion exchange resin particles. More preferably the granulating agent, if used, is in the range from about 5% to about 20% and most preferably in the range of about 10% to about 15% by weight of the uncoated drug-ion exchange resin particles. These granulating agents can be added during the formation of the drug-ion exchange resin complex either in the beginning, during the middle, or after substantial amount of complex formation has taken place. In the more preferred embodiment, the retardant is added after the formation of drug-ion exchange resin complex. Upon admixing, the drug-ion exchange resin complex particles with the granulating agent, the mixture is dried and milled appropriately. In some cases, the milling may be carried out before the complete drying of the complex and then again further drying followed by milling to obtain the desired size or other desired characteristics.

Pharmaceutically Acceptable Excipients

The compositions of the invention may be, e.g., a powder, powder for suspension (POS), powder in capsule, or suspension. The excipients for the composition are selected accordingly. Excipients in a suspension and/or ER POS may include suspending agents and/or thickening agent, wetting agents, and/or preservatives. Excipients are discussed in subsequent section.

The timing, pulse release compositions provided herein are generally dosed in the form of suspensions from powders admixed with a suspension base, preferably an aqueous suspension base. As used herein, an aqueous suspension refers to a suspension in which at least about 50% v/v of the liquid component of the suspension is water, preferably greater than about 60% w/v, greater than about 80% w/w, at least about 90% up to 100%. The suspension base may further contain comprises binders, diluents, salivating agents, surfactants, flavors, sweeteners, colorants, souring agents, viscolizers, glidants, chelating agents, lubricants, solubilizers, stabilizers, suspending agents, preservatives, cosolvents, anti-caking agents, buffers and the like or any combinations thereof. Examples of suitable binders include, but are not limited to, starch, pregelatinized starch, polyvinyl pyrrolidone, copovidone, cellulose derivatives, such as hydroxypropylmethyl cellulose, hydroxypropyl cellulose and carboxymethyl cellulose and their salts. Examples of suitable diluents include, but are not limited to, starch, microcrystalline cellulose, lactose, xylitol, mannitol, maltose, polyols, fructose, guar gum, sorbitol, magnesium hydroxide, dicalcium phosphate, coprocessed mannitol and calcium silicate and the like or any combinations thereof. Examples of lubricants include, but are not limited to, magnesium stearate, calcium stearate, stearic acid, talc, and sodium stearyl fumarate. Suitable glidants includes but are not limited to, colloidal silica, silica gel, precipitated silica, or combinations thereof. Suitable salivating agents include, but are not limited to, micronised polyethylene glycol, sodium chloride or precipitated micronised silica. Examples of solubilizers include, but are not limited to cetostearyl alcohol, cholesterol, diethanolamine, ethyl oleate, ethylene glycol palmitostearate, glycerin, glyceryl monostearate, isopropyl myristate, lecithin, medium-chain glyceride, monoethanolamine, oleic acid, propylene glycol, polyoxyethylene alkyl ether, polyoxyethylene castor oil glycoside, polyoxyethylene sorbitan fatty acid ester, polyethylene sorbitan fatty acid ester, polyoxyethylene stearate, propylene glycol alginate, sorbitan fatty acid ester, stearic acid, sunflower oil, triethanolmine, or combinations thereof. Souring agents include, but are not limited to, monosodium fumarate and/or citric acid. The compositions of the present invention may also include stabilizers such as, but not limited to, those described above under drug-resin complexes. Suitable chelating agents that may be employed have been discussed herein above. Suitable viscolizers include, but are not limited to, coprocessed microcrystalline cellulose such as but not limited to, Avicel RC591, Avicel CL-611, D-sorbitol solution, polyalkylene oxides such as, but not limited to polyethylene oxide; cellulose ethers such as, but not limited to hydroxyethyl cellulose, hydroxypropylcellulose, hydroxypropyl methyl cellulose, methyl cellulose, ethyl cellulose, sodium carboxy methylcellulose, calcium carboxymethyl cellulose, microcrystalline cellulose; gums such as but not limited to gum arabic alginates, agar, sodium alginate guar gum, locust bean, carrageenan, tara, gum arabic, tragacanth, pectin, xanthan, gellan, maltodextrin, galactomannan, pusstulan, laminarin, scleroglucan, gum arabic, inulin, karaya, whelan; polyols such as, but not limited to dipropylene glycol, polypropylene glycol, propylene glycol, polyethylene glycol (PEG), sorbitol and glycerol; carbopol, starch and starch-based polymers such as, but not limited to, pregelatinized starch, acrylic acid and methacrylic acid polymers, and esters thereof, maleic anhydride polymers; polymaleic acid; poly(acrylamides); poly(olefinic alcohol)s; poly(N-vinyl lactams); polyoxyethylated saccharides; polyoxazolines; polyvinylamines; polyvinylacetates; polyimines; povidone, vinylpyrrolidone/vinyl acetate copolymer and polyvinyl acetate, mixture of polyvinyl acetate and polyvinylpyrrolidone, chitin, cyclodextrin, gelatin, chitosan and the like or any mixtures thereof. Suitable surfactants include, but are not limited to, anionic, nonionic, cationic, and zwitterionic surfactants or a mixture thereof. The non-ionic surfactants employed in the composition may include, but are not limited to, ethoxylated fatty acid ester, ethoxylated fatty acid ethers, ethoxylated sorbitan ethers, ethoxylated alkyl-phenols, glycerol esters, glycerol sugar esters, polyoxyethyleneglycerol monolaurate, polyoxyethyleneglycerol monostearate, polyoxyethylene-20-cetyl stearate, polyoxyethylene-25-cetyl stearate, polyoxyethylene (25)-oxypropylene monostearate, polyoxyethylene-20-sorbitan monopalmitate, poly-oxyethylene-16-tert-octyl phenol, polyoxyethylene-20-cetyl ether, polyethylene glycol (1000) monocetyl ether, ethoxylated castor oil, polyoxyethylene sorbitol-lanolin derivatives, polyoxyethylene(25)propylene glycol stearate, polyoxyethylenesorbitol esters, polyoxyethylene-20-sorbitan monopalmitate, polyoxyethylene-16-tert-octylphenol, polyoxyethylene-20-cetyl ether, glycyeryl undecylenate and Polysorbate 60, capmul (medium chain glyceride), peceol (glyceryl monooleate), glyceryl laurate and glyceryl caprylate (Capmul MCM), PEG sorbitan fatty acid esters like PEG-20 sorbitan monolaurate (Tween 20), PEG-20 sorbitan monostearate (Tween 60), PEG-20 sorbitan monooleate (Tween 80), sorbitan fatty acid esters like sorbitan monolaurate (Span 20), glyceryl stearate (Cithrol GMS) or the like and mixtures thereof. Suitable cationic surfactants include, but are not limited to, quaternary ammonium compounds, alkylamidoamines and quaternary ester compounds, distearyl dimethyl ammonium chloride, dimyristyl dimethyl ammonium chloride, dipalmityl dimethyl ammonium chloride or the like and mixtures thereof. Suitable anionic surfactants include, but are not limited to, fatty alcohol sulfates, alpha olefin sulfonates, sulfosuccinates, phosphate esters, carboxylates, sarcosinates, alkyl benzene sulfonates, alkyl sulfonates, olefin sulfonates, alkyl ethersulfonates, glycerol ethersulfonates, α-methyl estersulfonates, sulfonic fatty acids, alkyl sulfates, fatty alcohol ethersulfates, glycerol ethersulfates, mixed hydroxy ethersulfates, monoglyceride (ether)sulfates, fatty acid amide (ether)sulfates, sulfosuccinates, sulfosuccinamates, sulfotriglycerides, amide soaps, ether carboxylic acids, isethionates, sarcosinates, taurides, alkyl oligoglycoside sulfates, alkyl (ether)phosphates or the like and mixtures thereof. Suitable zwitterionic surfactants employed include, but are not limited to, N-alkyl-N,N-dimethyl ammonium glycinates, for example cocoalkyl dimethyl ammonium glycinate, N-acyl aminopropyl-N,N-dimethyl ammonium glycinates, cocoacyl aminoethyl hydroxyethyl carboxymethyl glycinate or the like and mixtures thereof. Further, the composition of the present invention may further comprise a preservative such as but not limited to methyl parahydroxybenzoate, propyl parahydroxybenzoate and sodium benzoate. Suitable cosolvent that may be used includes, but is not limited to, ethanol and polyhydric alcohols such as, but not limited to, glycerin, propylene glycol, low molecular weight polyethylene glycols, and mixtures thereof. Further anti-caking agents that may be optionally incorporated include, but are not limited to, colloidal silicon dioxide, tribasic calcium phosphate, powdered cellulose, magnesium trisilicate, starch, and mixtures thereof. Suitable sweetening agent includes, but is not limited to, aspartame, *stevia* extract, *glycyrrhiza*, saccharine, saccharine sodium, acesulfame, sucralose, dipotassium glycyrrhizinate, galactose, fructose, high fructose corn syrup, dextrose, sucrose, sugar, maltose, partially hydrolyzed starch, corn syrup solids, sorbitol, xylitol, mannitol and the like or mixtures thereof. The compositions may comprise one or more natural and/or artificial flavors such as, but not limited to, mint flavour, orange flavour, lemon flavors, strawberry aroma, vanilla flavour, raspberry aroma, cherry flavor, tutti frutti flavor, magnasweet 135, key lime flavor, grape flavor, trusil art 511815, and fruit extracts and the like. Suitable colorants include, but are not limited to, pigments and dyes such as FD & C Red, FD & C Yellow, FD & C Green, and FD & C Blue and the like or combinations thereof.

The composition which forms a gastro-retentive RAFT having at least two trigger pulses, the composition comprise: (a) at least one biologically active moiety in an immediate release pulse release form; (b) at least one biologically active moiety in a delayed trigger release form; and (c) a RAFT system, wherein following oral ingestion, the composition provides a self-assembling gastro-retentive RAFT having entrapped therein, the at least one biologically active moiety of (a) and (b) and the gas generated in situ by the non-toxic gas generating agent, thereby providing a floating gastro-retentive RAFT having a dual pulse system wherein at least the second pulse is a trigger pulse and which retains the at least one biologically active moiety in the stomach for at least about 3 hours, provided that the composition does not include a gamma hydroxybutyrate and its salts, hydrates, tautomers, or solvates, or complexes thereof.

In certain embodiments, the composition comprises a pH sigmoidal delayed trigger system which comprises particles comprising: (a) at least one drug or drug-ion exchange resin complex; an organic acid coated with a reverse enteric coat; an optional gas generating agent; an optional bulking agent; and (b) Ammonio Methacrylate Copolymer, Type A (e.g., Eudragit RL), or Ammonio Methacrylate Copolymer, Type B (e.g., Eudragit RS) or both coat over the particles of (a), wherein said coat dissolves in the presence of the organic acid of (a), whereby following ingestion in the presence of acid a RAFT comprising a pH sigmoidal delayed trigger for the drug of (a) is formed. In certain embodiments, this pulse trigger system comprises at least one biologically active moiety in the form of drug-ion exchange resin complex (about 60% w/w, 10% w/w to 80% w/w of this pulse trigger system) plus: (i) a reverse enteric coated organic acid; (about 8%, 3 to 25% w/w) (ii) an optional gas generating agent (about 5%, 0 to 10% w/w); (iii) optionally a bulking agent (about 5%, 0 to 30% w/w); (iv) at least one pH-independent, water-insoluble, water-permeable diffusion barrier coating polymer, (e.g., Ammonio Methacrylate Copolymer, Type B), about 20%, 10 to 60% w/w) based on the weight of the trigger system.

In certain embodiments, this pulse trigger system comprises at least one biologically active moiety (about 10%, 5% w/w to 40% w/w of trigger system) plus (i) a reverse enteric coated organic acid; (about 3% w/w, 1% w/w to 10% w/w)) (ii) an optional gas generating agent (about 2%, 0 to 6% w/w) (iii) optionally a bulking agent (about 10%, 5% w/w to 25% w/w)) (iv) at least one pH-independent, water-insoluble, water-permeable diffusion barrier coating polymer, (e.g., Ammonio Methacrylate Copolymer, Type B), about 10%, 4% w/w to 40% w/w, of the trigger system.

In certain embodiments, the composition comprises an erosion delayed trigger system which comprises: at least one erosion barrier forming polymer; an optional gas generating agent; at least one drug or drug-ion exchange resin complex; and an optional bulking agent, whereby in the presence of stomach acid, a RAFT comprising the erosion delayed trigger system for the drug is formed. In certain embodiments, the erosion trigger system comprises (i) at least one biologically active moiety (e.g., an API, drug-ion exchange resin complex, or mixture thereof); (about 60%, 5% w/-80% w/w) (ii) at least one erosion barrier forming polymer selected from non-limiting list: HPMC, HEC, other cellulose ethers, guar gum; (about 15%, 5% w/w to 20% w/w) (iii) an optional gas generating agent (about 7% w/s, 0 to 15% w/w); (iv) optionally, bulking agent (about 15% w/w, 0 to 75% w/w) of the trigger system. Suitably, the active moiety and excipients are coated with the erodible barrier In certain embodiments, the composition has a pH, swelling delayed trigger system, comprising: (i) granules comprising at least one drug or drug-ion exchange resin complex, at least one pH modifier, at least one swelling agent, optionally a gas generating agent are coated with at least one enteric polymer, (ii) Reverse enteric coat over the granules of (i), whereby in the presence of stomach acid, a RAFT comprising the pH-swelling delayed trigger system for the drug of (i) is formed. In certain embodiments, a composition of the invention includes granules containing, at a minimum: (i) at least one biologically active moiety (e.g., a drug, drug-ion exchange resin complex, or mixture thereof), (about 40% w/w, 10% w/w to −75% w/w) (ii) at least one pH modifier (about 20% w/w, 5% w/w to 50% w/w); (iii) optionally a swelling agent (about 10% w/w, 5% w/w to 25% w/w) of the trigger system. The granules are coated with at least one enteric polymer and the coated granules are further coated with a reverse enteric polymer.

In certain embodiments, the composition has a swelling delayed trigger system, comprising: (i) granules comprising at least one drug or drug-ion exchange resin complex, at least one gelling agent, at least one swelling enhancer, an optional gas generating agent which generates gas in the presence of stomach acid, optionally, a bulking agent, and (ii) at least one water permeable diffusion barrier coating over the granules of (i), whereby in the presence of stomach acid, a RAFT comprising the swelling delayed trigger system for the drug of (i) is formed. In certain embodiments, a composition of the invention includes granules containing, at a minimum: (i) at least one biologically active moiety (drug-ion exchange resin complex, about 20% w/w of trigger, 10% w/w to 50% w/w) (ii) at least one gelling agent HPMCK4M (about 6% w/w, 3% w/w to 15% w/w); (iii) at least one swelling enhancer (about 20%, 10% w/w to 50% w/w) (iv) bulking agent, MCC (about 20% w/w, 10% w/w to 50% w/w). The granules are coated with at least one diffusion barrier PVA (about 15%, 10% w/w to 40% w/w) of the trigger system.

In certain embodiments, the composition has an osmosis delayed trigger system, comprising: (i) granules comprising at least one drug-ion exchange resin complex, at least one gelling agent, at least one osmogent, an optional gas generating agent which generates gas in the presence of stomach acid, an optional bulking agent and (ii) at least one water permeable diffusion barrier coating over the granules of (in), whereby in the presence of stomach acid, a RAFT comprising the osmosis delayed trigger system for the drug of (i) is formed. In certain embodiments, a composition of the invention includes granules containing, at a minimum: (i) at least one biologically active moiety (drug-ion exchange resin complex, about 20% w/w of trigger, 10% w/w to 50% w/w) (ii) at least one gelling agent HPMCK4M (about 8% w/w, 3% w/w to 15% w/w); (iii) at least one osmogent (about 20%, 10% w/w to 50% w/w) (iv) bulking agent, MCC (about 20% w/w, 10% w/w to 50% w/w) in the trigger system. The granules are coated with at least one diffusion barrier PVA (about 15% w/w, 10% w/w to 40% w/w).

In certain embodiments, the composition has two or more different delayed trigger pulse releases.

In certain embodiments, composition comprises two or more different drugs.

In certain embodiments, a Raft comprises two or more different drugs.

In certain embodiments, a Raft comprises the same drug in more than two different release forms.

In certain embodiments, the RAFT formed is initially at least about 15 mm in width as measured in vitro, e.g., using an assay describe in the examples and incorporated by reference herein.

In certain embodiments, the composition comprises two or more different RAFT systems.

In certain embodiments, the raft forming system comprises at least one crosslinkable polysaccharide, at least one crosslinking agent, and at least one gas generating agent which reacts with stomach acid to form a gas. In certain embodiments, the crosslinkable polysaccharide is a galactomannan selected from guar gum, fenugreek gum, or locust bean gum and the at least one cross-linking agent selected from borax, glutaraldehyde, and/or zirconium. In certain embodiments, the RAFT comprises the gelling agent, wherein the gelling agent is liquid at room temperature and gels at body temperature, and is selected from xyloglucan or a poloxamer. In certain embodiments, the RAFT comprises a cubic phase-forming lipid.

Uses

Suitably, the compositions of the invention contain GR Raft forming systems with trigger pulse release, which systems form in vivo in the presence of an acid (e.g., stomach or gastric acid). In certain embodiments, the compositions provide subjects with a timed, pulse release of one or more drug(s), with a first pulse in less than about 3 hours, a second pulse which is a trigger pulse, and optionally, or more additional pulses.

Without wishing to be bound by theory, it is believed that the upon reaction with the acid, a gas generating agent (and/or effervescence couple) in the composition forms a non-toxic gas which enables the GR RAFT containing the biologically active moiety to remain in the stomach for at least 2 hours, preferably, about 3 hours to 4 hours. It is believed this retention time is caused by the GR Raft exceeding the size of the pyloric valve for at least two hours. Thus, it is believed that the composition forms a GR Raft of at least about 15 mm in width, or more commonly at least about 20 mm in width for this length of time.

The compositions of the invention are well suited for treating subjects having a variety of conditions, disorders and/or diseases. In certain embodiments, the compositions provide increase gastric delivery and/or increase bioavailability of the active moieties in the composition. The compositions of the invention are well suited for treating subjects having a variety of conditions, disorders and/or diseases. one or more of allergic rhinitis, rheumatoid arthritis and related disorders, asthma, cancer, cardiovascular disease, inflammatory disorders, and ulcers. In certain embodiments, the compositions provide subjects with a modified release of one or more drug(s) in the GR Raft, which modified release profile is at least 2 hours, more preferably, at least 3 hours to 4 hours.

The words "comprise", "comprises", and "comprising", and "contain", "containing", and "contains" are to be interpreted inclusively rather than exclusively. The words "consist", "consisting", and its variants, are to be interpreted exclusively, rather than inclusively.

As used herein in reference to numeric values provided herein, the term "about" may indicate a variability of as much as 10%.

Examples

While the invention has been described with reference to exemplary embodiments, it will be understood by those skilled in the art that various changes may be made and equivalents may be substituted for elements thereof without departing from the scope of the invention. Details of the present invention, including its objects and advantages, are provided in the non-limiting exemplary illustrations below.

Example 1. Swelling as Trigger

TABLE 1

Composition of Glycopyrrolate GRPR suspension for suspension (POS)

| No. | Ingredients | Gm |
|---|---|---|
| | First pulse | |
| 1. | Glycopyrrolate HBr | 2.4 |
| 2. | Sodium polystyrene sulfonate | 4.8 |
| | Second pulse | |
| 3. | Glycopyrrolate HBr | 2.4 |
| 4. | Sodium polystyrene sulfonate | 4.8 |
| | PR carrier composition | |
| 5. | MCC | 7.5 |
| 6. | HPMC K4M | 2.5 |
| 7. | Cross-povidone | 7.5 |
| 8. | Calcium carbonate | 5 |
| 9. | Kollicoat ® SR 30D | 6 |
| 10. | PVPK30 | 1.5 |
| 11. | Triacetin | 1.0 |
| | GR carrier composition | |
| 12. | Iota carrageenan | 12 |
| 13. | Pectin | 12 |
| 14. | Calcium carbonate | 15 |
| 15. | Guar gum | 10 |
| 16. | Co-Povidone | 3 |
| | Other excipients | |
| 17. | HPMC low viscosity | 10.5 |
| 18. | Sucralose | 8.5 |
| 19. | Mannitol | 17 |
| 20. | Talc | 14 |
| 21. | Guar Gum | 1.6 |
| 22. | Banana flavor | 8.0 |

I. Preparation of Drug-Ion Exchange Resin Complex

Weighed quantity of Glycopyrrolate HBr is dissolved in 1000 ml water. Weight quantity of the resin is added to drug solution under stirring and stirring is continued further for a period of 4 hr. Drug-resin complex is isolated by filtration and dried at 60° C. Drug-resin complex is passed through #60 screen.

II. Preparation of PR Carrier Composition

Weighed quantity of drug-ion exchange resin complex for second pulse is mixed with weighed quantities of MCC, HPMCK4M, cros-povidone, calcium carbonate for 15 min and granulated using 10% w/v solution of PVP K30. Wet granules are dried at 60° C. and passed through #40 screen. Triacetin is added in purified water under stirring and continue stirring to get clear solution. Triacetin solution is added gradually to Kollicoat® ® SR30D dispersion under stirring and continue stirring for 1 hr. The coating dispersion is screened through sieve #40. The dried granules are coated using the prepared dispersion and stirring is continued throughout the coating process. Coating is performed in Fluid Bed Coater and coated complex is dried at 60° C. Coated complex is passed through #40 screen.

III. Preparation of GR Carrier Composition

Weighed quantity of drug-ion exchange resin complex for first pulse is mixed with weighed quantities of carrageenan iota, carrageenan kappa, potassium citrate, calcium carbonate are mixed for 15 min and granulated using 10% w/v solution of Co-povidone. Wet granules are dried at 60° C. and passed through #40 screen.

IV. The granules of step II, and granules of step III are mixed with weighed and screened (#40) quantities of HPMC K100LV, banana flavor, talc, sodium benzoate, mannitol and sucralose for 15 min. For 4.8 mg Glycopyrrolate HBr equivalent dose, 160 mg of POS is to be reconstituted using 2 gm purified water at the time of administration.

In-Vitro Testing

I. Onset and Duration of Duration of Floating

Amount of suspension equivalent to 4.8 mg Glycopyrrolate HBr dose is added to 500 ml SGF without enzyme. The time required for raft to float and duration of floating are anticipated:

| | |
|---|---|
| Onset of floating (minutes) | <20 |
| Duration of floating (hours) | 12 |

II. Resiliency of the Raft

Amount of suspension equivalent to 4.8 mg Glycopyrrolate HBr dose is added to 500 ml SGF without enzyme 0.1N HCl solution. Then it is subject to agitation using mechanical shaker set at 37° C. and 75 rpm. Anticipated Observation: The raft retains integrity for a period of 12 hours III. In Vitro Release Study Dissolution studies are performed using USP Apparatus Type II set at 50 rpm and 37° C. and 500 ml SGF without enzyme as medium. The anticipated release is illustrated in FIG. 2.

Example 2. Swelling Plus Osmosis as Trigger

TABLE 2

Composition of Promethazine GRPR POS

| No. | Ingredients | Gm |
|---|---|---|
| | First pulse | |
| 1. | Promethazine HCl | 12.5 |
| 2. | Polacrilex resin (Amberlite ® IRP64) | 25.0 |
| | Second pulse | |
| 3. | Promethazine HCl | 12.5 |
| 4. | Polacrilex resin (Amberlite ® IRP64) | 25.0 |
| | PR carrier composition | |
| 5. | HPMC K4M | 10 |
| 6. | MCC | 10 |
| 7. | Mannitol | 30 |
| 8. | Calcium carbonate | 15 |
| 9. | Kollicoat ® SR 30D | 15 |

TABLE 2-continued

Composition of Promethazine GRPR POS

| No. | Ingredients | Gm |
|---|---|---|
| 10. | Triacetin | 3 |
| 11. | PVPK30 | 5 |
| | GR carrier composition | |
| 9. | Iota carrageenan | 25 |
| 10. | Pectin | 15 |
| 11. | Gelan gum | 15 |
| 12. | Calcium carbonate | 30 |
| 13. | Polyox | 5 |
| 14. | Co-Povidone | 5 |
| | Other excipients | |
| 14. | HPMC low viscosity | 10.5 |
| 15. | Sucralose | 8.5 |
| 16. | Mannitol | 17 |
| 17. | Talc | 14 |
| 18. | Guar Gum | 1.5 |
| 19. | Banana flavor | 8.5 |

I. Preparation of Drug-Ion Exchange Resin Complex

Weighed quantity of Promethazine HCl is dissolved in 1000 ml water. Weight quantity of the resin is added to drug solution under stirring and stirring is continued further for a period of 4 hr. Drug-resin complex is isolated by filtration and dried at 60° C. Drug-resin complex is passed through #60 screen.

II. Preparation of PR Carrier Composition

Weighed quantity of drug-ion exchange resin complex for second pulse is mixed with weighed quantities of MCC, HPMCK4M, mannitol, calcium carbonate for 15 min and granulated using 10% w/v solution of PVP K30. Wet granules are dried at 60° C. and passed through #40 screen. Triacetin is added in purified water under stirring and continue stirring to get clear solution. Triacetin solution is added gradually to Kollicoat® SR30D dispersion under stirring and continue stirring for 1 hr. The coating dispersion is screened through sieve #40. The dried granules are coated using the prepared dispersion and stirring is continued throughout the coating process. Coating is performed in Fluid Bed Coater and coated complex is dried at 60° C. Coated complex is passed through #40 screen.

III. Preparation of GR Carrier Composition

Weighed quantity of drug-ion exchange resin complex for first pulse is mixed with weighed quantities of carrageenan iota, carrageenan kappa, potassium citrate, calcium carbonate are mixed for 15 min and granulated using 10% w/v solution of Co-povidone. Wet granules are dried at 60° C. and passed through #40 screen.

IV. The granules of step II, and granules of step III are mixed with weighed and screened (#40) quantities of HPMC K100LV, banana flavor, talc, sodium benzoate, mannitol and sucralose for 15 min. For 25 mg Promethazine HCl equivalent dose, 318 mg of POS is to be reconstituted using 2 gm purified water at the time of administration.

In-Vitro Testing

I. Onset and Duration of Duration of Floating

Amount of reconstituted suspension equivalent to 25 mg Promethazine HCl is added to 500 ml SGF without enzyme. The time required for raft to float and duration of floating are anticipated.

| | |
|---|---|
| Onset of floating (minutes) | <20 |
| Duration of floating (hours) | 12 |

II. Resiliency of the Raft

Amount of reconstituted suspension equivalent to 25 mg Promethazine HCl dose is added to 500 ml SGF without enzyme 0.1N HCl solution. Then it is subjected to agitation using mechanical shaker set at 37° C. and 75 rpm. Anticipated observation: The raft retains integrity for a period of 12 hours.

III. In Vitro Release Study

Dissolution studies are performed using USP Apparatus Type II set at 50 rpm and 37° C. and 500 ml SGF without enzyme as medium using Amount of reconstituted suspension equivalent to 25 mg Promethazine HCl dose. The anticipated dissolution curve is provided in FIG. 3.

Example 3. pH as Trigger, Sigmoidal Release System for Generating Second Pulse

TABLE 3

Composition of GRPR POS

| No. | Ingredients | Gm |
|---|---|---|
| | First pulse | |
| 1. | Propranolol HCl | 40 |
| 2. | Sodium polystyrene sulfonate | 80 |
| | Second pulse | |
| 3. | Propranolol HCl | 40 |
| 4. | Sodium polystyrene sulfonate | 80 |
| | PR carrier composition | |
| 5. | Fumaric acid | 10 |
| 6. | MCC | 80 (20 + 60) |
| 7. | PVP K30 | 10 (2 + 8) |
| 8. | Eudragit ®EPO | 6 |
| 9. | Triacetin | 6 |
| 10. | Eudragit ® RS | 34 |
| | GR carrier composition | |
| 11. | Iota carrageenan | 50 |
| 12. | Pectin | 50 |
| 13. | Gelan gum | 40 |
| 14. | Calcium carbonate | 75 |
| 15. | Sodium bicarbonate | 30 |
| 16. | Co-Povidone | 15 |
| | Other excipients | |
| 17. | HPMC low viscosity | 10.5 |
| 18. | Sucralose | 8.5 |
| 19. | Mannitol | 17 |
| 20. | Talc | 14 |
| 21. | Guar Gum | 1.5 |
| 22. | Banana flavor | 8.5 |
| 23. | Sodium benzoate | 2.0 |

I. Preparation of Drug-Ion Exchange Resin Complex

Weighed quantity of Propranolol HCl is dissolved in 1000 ml water. Weight quantity of the resin is added to drug solution under stirring and stirring is continued further for a period of 4 hr. Drug-resin complex is isolated by filtration and dried at 60° C. Drug-resin complex is passed through #60 screen.

II. Preparation of PR Carrier Composition

Weighed quantity of fumaric acid and 20 gm MCC are mixed and granulated using aqueous solution containing 2 gm of copovidone. Wet granules are dried at 60° C. and passed through #40 screen. Granules are coated using Eudragit EPO plasticized using triacetin. Coated granules are passed through #40 screen. These granules are mixed with weighed quantities of drug-ion exchange resin complex for second pulse and calcium carbonate for 15 min and granulated using 10% w/v solution of copovidone. Wet granules are dried at 60° C. and passed through #40 screen. Granules are coated using Eudragit RS plasticized using triacetin. Coating is performed in Fluid Bed Coater and coated complex is dried at 60° C. Coated granules are passed through #40 screen.

III. Preparation of GR Carrier Composition

Weighed quantities of carrageenan iota, pectin, gelan gum, sodium bicarbonate, calcium carbonate are mixed for 15 min and granulated using 10% w/v solution of Co-povidone. Wet granules are dried at 60° C. and passed through #40 screen.

IV. Weighed quantities of drug-ion exchange resin complex of step I, PR granules of step II, and granules of step III are mixed with weighed and screened (#40) quantities of HPMC K100LV, banana flavor, talc, sodium benzoate, mannitol and sucralose for 15 min. For 80 mg propranolol HCl, 708 mg of POS is to be reconstituted using 5 gm purified water at the time of administration.

In-Vitro Testing

I. Onset and Duration of Duration of Floating

Amount of reconstituted suspension equivalent to 80 mg propranolol HCl is added to 500 ml SGF without enzyme. The time required for raft to float and duration of floating are anticipated:

| Onset of floating (minutes) | <20 |
|---|---|
| Duration of floating (hours) | 12 |

II. Resiliency of the Raft

Amount of reconstituted suspension equivalent to 80 mg Propranolol HCl dose is added to 500 ml SGF without enzyme 0.1N HCl solution. Then it is subjected to agitation using mechanical shaker set at 37° C. and 75 rpm. Anticipated observation: The raft retains integrity for a period of 12 hours.

III. In Vitro Release Study

Dissolution studies are performed using USP Apparatus Type II set at 50 rpm and 37° C. and 500 ml SGF without enzyme as medium using Amount of reconstituted suspension equivalent to 25 mg Promethazine HCl dose. The anticipated dissolution curve is provided in FIG. 4.

Example 4. Erosion as Trigger

TABLE 4

Composition of GRPR powder for suspension (POS)

| No. | Ingredients | Gm |
|---|---|---|
| | First pulse | |
| 1. | Pregabalin | 50 |
| 2. | Cholestyramine | 200 |
| | Second pulse | |
| 3. | Pregabalin | 50 |
| 4. | Cholestyramine | 200 |
| | PR carrier composition | |
| 5. | MCC | 75 |
| 6. | PVP K30 | 9 |
| 7. | Calcium carbonate | 30 |
| 8. | HPMC K100LV | 60 |
| 9. | PEG400 | 6 |

TABLE 4-continued

Composition of GRPR powder for suspension (POS)

| No. | Ingredients | Gm |
|---|---|---|
| | GR carrier composition | |
| 10. | Iota carrageenan | 100 |
| 11. | Pectin | 100 |
| 12. | Sodium bicarbonate | 75 |
| 13. | Calcium carbonate | 150 |
| 14. | HPMC K100LV | 75 |
| | Other excipients | |
| 15. | HPMC low viscosity | 21 |
| 16. | Sucralose | 15 |
| 17. | Mannitol | 40 |
| 18. | Talc | 14 |
| 19. | Guar Gum | 10 |
| 20. | Banana flavor | 8.0 |
| 21 | Sodium benzoate | 2.0 |

I. Preparation of Drug-Ion Exchange Resin Complex

Weighed quantity of Pregabalin is dissolved in 1000 ml water. Weight quantity of the resin is added to drug solution under stirring and stirring is continued further for a period of 4 hr. Drug-resin complex is isolated by filtration and dried at 60° C. Drug-resin complex is passed through #60 screen.

II. Preparation of PR Carrier Composition

Weighed quantity of drug-ion exchange resin complex for second pulse is mixed with weighed quantities of MCC, HPMC K4M, calcium carbonate for 15 min and granulated using 10% w/v solution of PVP K30. Wet granules are dried at 60° C. and passed through #40 screen. Dried granules are coated in fluidized bed processor using HPMC K100LV plasticized using PEG 400. Coated granules are dried at 60° C. Coated granules are passed through #30 screen.

III. Preparation of GR Carrier Composition

Weighed quantities of carrageenan iota, pectin, sodium bicarbonate, calcium carbonate, and HPMC K100LV are mixed for 15 min and granulated. Wet granules are dried at 60° C. and passed through #40 screen.

IV. Weighed quantity of drug-ion exchange resin complex for first pulse, the granules of step II, and granules of step III are mixed with weighed and screened (#40) quantities of HPMC K100LV, banana flavor, talc, sodium benzoate, mannitol and sucralose for 15 min. For 300 mg Pregabalin equivalent dose, 3870 mg of POS is to be reconstituted using 30 gm purified water at the time of administration.

In-Vitro Testing

I. Onset and Duration of Duration of Floating

Amount of reconstituted suspension equivalent to 300 mg Pregabalin is added to 500 ml SGF without enzyme. The time required for raft to float and duration of floating are anticipated as follows:

| | |
|---|---|
| Onset of floating (minutes) | <15 |
| Duration of floating (hours) | 12 |

II. Resiliency of the Raft

Amount of reconstituted suspension equivalent to 300 mg Pregabalin is added to 500 ml SGF without enzyme 0.1N HCl solution. Then it is subjected to agitation using mechanical shaker set at 37° C. and 75 rpm. Anticipated observation: The raft retains integrity for a period of 12 hours.

Example 5. pH as Trigger, Sigmoidal Release System for Generating Second Pulse

I. Preparation of Melt Granules

TABLE 5

| Ingredients | Gm |
|---|---|
| Valsartan | 100 |
| PEG 8000 | 50 |
| Poloxamer 407 | 50 |
| Microcrystalline cellulose | 100 |

Weighed quantity of PEG 8000 and Poloxamer 407 are molten together. Weighed quantity of valsartan is added to molten mass under mixing and mixing is continued for 5 min more. Weighed quantity of microcrystalline cellulose is added under mixing. The entire mass is allowed to cool to ambient temperature under continuous mixing. The cooled mass is passed through #20 screen.

TABLE 6

Composition of GRPR POS

| No. | Ingredients | Gm |
|---|---|---|
| | First pulse | |
| 1. | Valsartan melt granules | 30 |
| | PR carrier composition | |
| 2. | Fumaric acid | 10 |
| 3. | Valsartan melt granules | 210 |
| 6. | MCC | 80 (20 + 60) |
| 7. | PVP K30 | 10 (2 + 8) |
| 8. | Eudragit ® EPO | 6 |
| 9. | Triacetin | 6 (1 + 5) |
| 10. | Eudragit ® RS | 30 |
| | GR carrier composition | |
| 11. | Iota carrageenan | 30 |
| 12. | Pectin | 40 |
| 13. | Gelan gum | 20 |
| 14. | Calcium carbonate | 75 |
| 15. | Sodium bicarbonate | 50 |
| 16. | Co-Povidone | 15 |
| | Other excipients | |
| 17. | HPMC low viscosity | 10.5 |
| 18. | Sucralose | 8.5 |
| 19. | Mannitol | 17 |
| 20. | Talc | 14 |
| 21. | Guar Gum | 1.5 |
| 22. | Banana flavor | 8.5 |
| 23. | Sodium benzoate | 2.0 |

II. Preparation of PR Carrier Composition

Weighed quantity of fumaric acid and 20 gm MCC are mixed and granulated using aqueous solution containing 2 gm of copovidone. Wet granules are dried at 60° C. and passed through #40 screen. Granules are coated using Eudragit EPO plasticized using triacetin. Coated granules are passed through #40 screen. These granules are mixed with weighed quantities of vasartan melt granules for second pulse, MCC and calcium carbonate for 15 min and granulated using 10% w/v solution of copovidone. Wet granules are dried at 60° C. and passed through #40 screen. Granules are coated using Eudragit® RS plasticized using triacetin. Coating is performed in Fluid Bed Coater and coated complex is dried at 60° C. Coated granules are passed through #40 screen.

III. Preparation of GR Carrier Composition

Weighed quantities of carrageenan iota, pectin, gelan gum, sodium bicarbonate, calcium carbonate are mixed for 15 min and granulated using 10% w/v solution of Co-povidone. Wet granules are dried at 60° C. and passed through #40 screen.

IV. Weighed quantities of melt granules for first pulse, PR granules of step II, and granules of step III are mixed with weighed and screened (#40) quantities of HPMC K100LV, banana flavor, talc, sodium benzoate, mannitol and sucralose for 15 min. For 80 mg valsartan, 674 mg of POS is to be reconstituted using 3 gm purified water at the time of administration.

In-Vitro Testing

I. Onset and Duration of Duration of Floating

Amount of reconstituted suspension equivalent to 80 mg valsartan is added to 500 ml SGF without enzyme. The time required for raft to float and duration of floating are anticipated.

| | |
|---|---|
| Onset of floating (minutes) | <20 |
| Duration of floating (hours) | 12 |

II. Resiliency of the Raft

Amount of reconstituted suspension equivalent to 80 mg valsartan is added to 500 ml SGF without enzyme 0.1N HCl solution. Then it is subjected to agitation using mechanical shaker set at 37° C. and 75 rpm. Anticipated observation: The raft retains integrity for a period of 12 hours.

III. In Vitro Release Study

Dissolution studies are performed using USP Apparatus Type II set at 50 rpm and 37° C. and 500 ml SGF without enzyme as medium using amount of reconstituted suspension equivalent to 80 mg valsartan. The anticipated dissolution curve is provided in FIG. 5.

Example 6. pH as Trigger, Sigmoidal Release System for Generating Second Pulse

TABLE 7

Composition of GRPR POS

| No. | Ingredients | Gm |
|---|---|---|
| | First pulse | |
| 1. | Propranolol HCl | 40 |
| 2. | MCC | 40 |
| 3. | Co-povidone | 5 |
| | PR carrier composition | |
| 4. | Succinic acid | 10 |
| 5. | Propranolol HCl | 40 |
| 6. | MCC | 40 (20 + 20) |
| 7. | PVP K30 | 10 (2 + 8) |
| 8. | Eudragit ® EPO | 6 |
| 9. | Triacetin | 6 (1 + 5) |
| 10. | Eudragit ® RS | 30 |
| | GR carrier composition | |
| 11. | Iota carrageenan | 25 |
| 12. | Pectin | 25 |
| 13. | Gelan gum | 20 |
| 14. | Calcium carbonate | 50 |
| 15. | Sodium bicarbonate | 30 |
| 16. | Co-Povidone | 15 |

TABLE 7-continued

Composition of GRPR POS

| No. | Ingredients | Gm |
|---|---|---|
| | Other excipients | |
| 17. | HPMC low viscosity | 10.5 |
| 18. | Sucralose | 8.5 |
| 19. | Mannitol | 17 |
| 20. | Talc | 14 |
| 21. | Guar Gum | 1.5 |
| 22. | Banana flavor | 8.5 |
| 23. | Sodium benzoate | 2.0 |

I. Preparation of Drug Granules

Weighed quantity of Propranolol HCl is mixed with MCC and granulated using 10% w/v solution of copovidone. Wet granules are dried at 60° C. and passed through #40 screen.

II. Preparation of PR Carrier Composition

Weighed quantity of succinic acid and 20 gm MCC are mixed and granulated using aqueous solution containing 2 gm of copovidone. Wet granules are dried at 60° C. and passed through #40 screen. Granules are coated using Eudragit EPO plasticized using triacetin. Coated granules are passed through #40 screen. These granules are mixed with weighed quantities of drug-ion exchange resin complex for second pulse and calcium carbonate for 15 min and granulated using 10% w/v solution of copovidone. Wet granules are dried at 60° C. and passed through #40 screen. Granules are coated using Eudragit RS plasticized using triacetin. Coating is performed in Fluid Bed Coater and coated complex is dried at 60° C. Coated granules are passed through #40 screen.

III. Preparation of GR Carrier Composition

Weighed quantities of carrageenan iota, pectin, gelan gum, sodium bicarbonate, calcium carbonate are mixed for 15 min and granulated using 10% w/v solution of Co-povidone. Wet granules are dried at 60° C. and passed through #40 screen.

IV. Weighed quantities of drug granules of step I, PR granules of step II, and granules of step III are mixed with weighed and screened (#40) quantities of HPMC K100LV, banana flavor, talc, sodium benzoate, mannitol and sucralose for 15 min. For 80 mg propranolol HCl, 454 mg of POS is to be reconstituted using 5 gm purified water at the time of administration.

In-Vitro Testing

I. Onset and Duration of Duration of Floating

Amount of reconstituted suspension equivalent to 80 mg Propranolol HCl is added to 500 ml SGF without enzyme. The time required for raft to float and duration of floating are anticipated to be:

| | |
|---|---|
| Onset of floating (minutes) | <10 |
| Duration of floating (hours) | 12 |

II. Resiliency of the Raft

Amount of reconstituted suspension equivalent to 80 mg Propranolol HCl dose is added to 500 ml SGF without enzyme 0.1N HCl solution. Then it is subjected to agitation using mechanical shaker set at 37° C. and 75 rpm. Anticipated observation: The raft retains integrity for a period of 12 hours Example 7: pH Plus Swelling as Trigger

TABLE 8

Composition of GRPR POS

| No. | Ingredients | Gm |
|---|---|---|
| | Tramadol hydrochloride in first pulse | |
| 1. | Tramadol hydrochloride | 5 |
| 2. | Microcrystalline cellulose | 5 |
| 3. | Co-povidone | 0.5 |
| | PR carrier composition | |
| 4. | Tramadol hydrochloride | 95 |
| 5. | Dicalcium phosphate dihydrate | 50 |
| 7. | PVP K30 | 5.5 |
| 8. | Eudragit ® L100-55 | 30 |
| 9. | Eudragit ® EPO | 45 |
| 10. | Triethyl citrate | 6 |
| | GR carrier composition | |
| 11. | Iota carrageenan | 20 |
| 12. | Pectin | 25 |
| 13. | Gelan gum | 10 |
| 14. | Calcium carbonate | 25 |
| 15. | Sodium bicarbonate | 30 |
| 16. | HPMC K4M | 5 |
| | Other excipients | |
| 17. | HPMC low viscosity | 10 |
| 18. | Sucralose | 8 |
| 19. | Mannitol | 15 |
| 20. | Talc | 14 |
| 21. | Guar Gum | 1.5 |
| 22. | Banana flavor | 8.5 |
| 23. | Sodium benzoate | 1.0 |

I. Tramadol Hydrochloride Granules in First Pulse

Weighed quantity of Tramadol hydrochloride is mixed MCC for 15 min and granulated using 10% w/v solution of co-povidone in water. Wet granules are dried at 60° C. Dried granules are passed through #40 screen.

II. Preparation of PR Carrier Composition

Weighed quantity of tramadol hydrochloride in second pulse is mixed with weighed quantity of dicalcium phosphate dehydrate and granulated using PVP solution. Granules are dried and passed through #60 screen. Granules are coated with Eudragit L100-55 plasticized using triethyl citrate. Coated granules are further coated with Eudragit EPO plasticized by TEC. Coated granules are passed through #40 screen.

III. Preparation of GR Carrier Composition

Weighed quantities of carrageenan iota, pectin, gelan gum, calcium carbonate, sodium bicarbonate, HPMC K4M are mixed for 15 min and granulated. Wet granules are dried at 60° C. and passed through #40 screen.

IV. The granules of step I, coated granules of step III, and granules of step IV are mixed with weighed and screened (#40) quantities of HPMC K100LV, banana flavor, talc, sodium benzoate, mannitol and sucralose for 15 min For 100 mg tramadol hydrochloride, 415 mg of POS is to be reconstituted using 3 gm purified water at the time of administration.

In-Vitro Testing

I. Onset and Duration of Duration of Floating

Amount of reconstituted suspension equivalent to 100 mg tramadol hydrochloride is added to 500 ml SGF without enzyme. The time required for raft to float and duration of floating are anticipated as follows.

| | |
|---|---|
| Onset of floating (minutes) | <5 |
| Duration of floating (hours) | 12 |

II. Resiliency of the Raft

Amount of reconstituted suspension equivalent to 100 mg tramadol hydrochloride is added to 500 ml SGF without enzyme 0.1N HCl solution. Then it is subjected to agitation using mechanical shaker set at 37° C. and 75 rpm. Anticipated observation: The raft retains integrity for a period of 12 hours.

In Vitro Release Study

Dissolution studies are performed using USP Apparatus Type II set at 50 rpm and 37° C. and 500 ml SGF without enzyme as medium. Amount of reconstituted suspension equivalent to 100 mg tramadol hydrochloride is added. Sampling points: 1, 2, 3, 4, 6, 8, 10, 12 hours. The anticipated dissolution curve is provided in FIG. 6.

All patents, patent publications, and other publications listed in this specification, are incorporated herein by reference. U.S. Patent Application No. 62/607,141, filed Dec. 18, 2017, is incorporated by reference. While the invention has been described with reference to a particularly preferred embodiment, it will be appreciated that modifications can be made without departing from the spirit of the invention. Such modifications are intended to fall within the scope of the appended claims.

The invention claimed is:

1. An orally administrable drug powder composition which forms a gastro-retentive RAFT having at least two trigger pulses, the composition comprising:
   (a) at least one drug in a first trigger pulse release form which releases in less than 3 hours post-dosing;
   (b) at least one drug in at least one delayed trigger release form which provides the trigger release after the first pulse release of (a), wherein at least one drug in the delayed trigger release form is in drug ion exchange resin complex granules which are optionally coated with at least one diffusion barrier coating or a reverse enteric polymer coating;
   (c) a self-assembling gastro-retentive RAFT forming system which comprises at least one non-toxic gas generating agent which forms a gas in situ in the presence of stomach acid and one or more of: at least one gelling agent, at least one swelling enhancer, at least one erosion barrier forming polymer, at least one an organic acid coated with a reverse enteric coat, at least a barrier coating polymer over the drug-ion exchange resin complex, and/or at least a reverse enteric coat polymer over the drug ion exchange resin complex, and
      wherein following oral ingestion and exposure to stomach acid, the composition provides a self-assembling gastro-retentive RAFT having entrapped therein, the at least one delayed trigger release form of (b) and the gas generated in situ by the non-toxic gas generating agent, thereby providing a floating gastro-retentive RAFT which retains the at least one drug of (b) in the stomach for at least about 3 hours and which retains the floating gastro-retentive RAFT form following the delayed trigger release,
   provided that the composition does not include a gamma hydroxybutyrate, or a gamma hydroxybutyrate salt, hydrate, tautomer, or solvate, or complex thereof.

2. The orally administrable powder composition according to claim 1, wherein the composition comprises a pH sigmoidal delayed trigger system which comprises particles comprising:
(i) at least one drug, drug-ion exchange resin complex, or mixture thereof; an organic acid coated with a reverse enteric coat; an optional gas generating agent; an optional bulking agent; and
(ii) at least one pH-independent, water-insoluble, water-permeable diffusion barrier coating polymer over the particles of (i), wherein said coat dissolves in the presence of the organic acid of (i), whereby following ingestion in the presence of acid, the RAFT which is formed comprises the pH sigmoidal delayed trigger for the drug.

3. The orally administrable powder composition according to claim 1, wherein the composition comprises an erosion delayed trigger system which comprises: at least one erosion barrier forming polymer; an optional gas generating agent; at least one drug, drug-ion exchange resin complex, or combination thereof; and an optional bulking agent, whereby in the presence of stomach acid, the RAFT which is formed comprises the erosion delayed trigger system.

4. The orally administrable powder composition according to claim 1, wherein the composition has a pH-swelling delayed trigger system, comprising: (i) granules comprising at least one drug, drug-ion exchange complex, or mixture thereof, at least one pH modifier, at least one swelling agent, optional gas generating agent coated with at least one enteric polymer, (ii) optionally, a reverse enteric polymer coat over the granules of (i), whereby in the presence of stomach acid, the RAFT which is formed comprises the pH-swelling delayed trigger system.

5. The orally administrable powder composition according to claim 1, wherein the composition has a swelling delayed trigger system, comprising: (i) granules comprising at least one drug or any drug salt or drug-ion exchange complex, at least one gelling agent, at least one swelling enhancer, an optional gas generating agent which generates gas in the presence of stomach acid, and, optionally, a bulking agent, and (ii) at least one water permeable diffusion barrier coating over the granules of (i), whereby in the presence of stomach acid, the RAFT which is formed comprises the swelling delayed trigger system.

6. The orally administrable powder composition according to claim 1, wherein the composition has an osmosis delayed trigger system, comprising: (i) granules comprising at least one drug or any drug salt or drug-ion exchange resin complex, at least one gelling agent, at least one osmogent, an optional gas generating agent which generates gas in the presence of stomach acid, and, an optional bulking agent and (ii) at least one water permeable diffusion barrier coating over the granules of (i), whereby in the presence of stomach acid, the RAFT formed comprises the osmosis delayed trigger system.

7. The orally administrable powder composition according to claim 1, wherein the RAFT has two or more different delayed trigger pulse releases.

8. The orally administrable powder composition according to claim 1, wherein the composition comprises two or more different drugs.

9. The orally administrable powder composition according to claim 1, wherein the RAFT comprises two or more different drugs.

10. The orally administrable powder composition according to claim 1, wherein the RAFT comprises the same drug in more than two different release forms.

11. The orally administrable powder composition according to claim 1, wherein the composition comprises two or more different RAFT systems.

12. The orally administrable drug composition according to claim 1, wherein the RAFT system comprises the gelling agent, wherein the gelling agent is liquid at room temperature and gels at body temperature, and is xyloglucan or a poloxamer.

13. The orally administrable drug composition according to claim 1, wherein the gas-generating agent is selected from carbonates or bicarbonates of an alkali or alkaline earth metal, sulfites, or combinations thereof, or combinations thereof with an acid source which create a gas-generating couple.

14. The orally administrable drug composition according to claim 13, wherein the carbonate or bicarbonate of an alkali or alkaline earth metal are selected from potassium carbonate, potassium bicarbonate, sodium carbonate, sodium bicarbonate, calcium carbonate, sodium glycine carbonate, magnesium carbonate, or aluminum carbonate.

15. The orally administrable drug composition according to claim 1, wherein the drug is useful for treating one or more of allergic rhinitis, rheumatoid arthritis and related disorders, asthma, cancer, cardiovascular disease, inflammatory disorders, or ulcers.

16. A method for delivering a modified release drug to a human patient, the method comprising dosing the patient with the composition according to claim 15 comprising the modified release drug.

17. An orally administrable powder composition which forms a gastro-retentive RAFT having at least two trigger pulses, the composition comprising:
(a) at least one drug in a first trigger pulse release form which releases in less than 3 hours post-dosing;
(b) at least one drug in at least one delayed trigger release form which provides the trigger release after the first pulse release of (a), wherein at least one drug in the delayed trigger release form is in drug-ion exchange resin complex granules which are optionally coated with at least one coating;
(c) a self-assembling gastro-retentive RAFT forming system which comprises at least one crosslinkable polysaccharide, at least one crosslinking agent, and at least one non-toxic gas generating agent which reacts with stomach acid to form a gas, and
wherein following oral ingestion and exposure to stomach acid, the composition provides a self-assembling gastro-retentive RAFT having entrapped therein the at least one delayed trigger release form of (b) and the gas generated in situ by the non-toxic gas generating agent, whereby the floating gastro-retentive RAFT retains the at least one drug of (b) in the stomach for at least about 3 hours and which retains the RAFT form following the delayed trigger release,
provided that the composition does not include a gamma hydroxybutyrate, or a gamma hydroxybutyrate salt, hydrates, tautomer, or solvates, or complexes thereof.

18. The orally administrable drug composition according to claim 17, wherein the crosslinkable polysaccharide is a galactomannan selected from guar gum, fenugreek gum, or locust bean gum and the at least one cross-linking agent is one or more of borax, glutaraldehyde, and/or zirconium.

* * * * *